US012691446B2

(12) United States Patent
Jimenez-Zenteno et al.

(10) Patent No.: US 12,691,446 B2
(45) Date of Patent: Jul. 28, 2026

(54) SYSTEM FOR CAPTURING AND DETECTING SPECIES PRESENT IN A BIOLOGICAL FLUID

(71) Applicants: SMARTCATCH, Toulouse (FR); CENTRE NATIONAL DE LA RECHERCHE SCIENTIFIQUE, Paris (FR); INSTITUT NATIONAL DES SCIENCES APPLIQUEES DE TOULOUSE, Toulouse Cedex (FR); INSTITUT NATIONAL POLYTECHNIQUE DE TOULOUSE, Toulouse (FR); UNIVERSITE TOULOUSE III—PAUL SABATIER, Toulouse (FR)

(72) Inventors: Alejandro Kayum Jimenez-Zenteno, Toulouse (FR); David Bourrier, Ramonville St Agne (FR); Elise Bou, Toulouse (FR); Aline Cerf, Saint Orens de Gameville (FR); Hervé Aubert, Toulouse (FR); Christophe Vieu, Auzeville Tolosane (FR); Bernard Malavaud, Toulouse (FR)

(73) Assignees: SMARTCATCH, Toulouse (FR); CENTRE NATIONAL DE LA RECHERCHE SCIENTIFIQUE, Paris (FR); INSTITUT NATIONAL DES SCIENCES APPLIQUEES DE TOULOUSE, Toulouse (FR); INSTITUT NATIONAL POLYTECHNIQUE DE TOULOUSE, Toulouse (FR); UNIVERSITE TOULOUSE III—PAUL SABATIER, Toulouse (FR)

( * ) Notice: Subject to any disclaimer, the term of this patent is extended or adjusted under 35 U.S.C. 154(b) by 824 days.

(21) Appl. No.: 17/777,482

(22) PCT Filed: Nov. 19, 2020

(86) PCT No.: PCT/FR2020/052138
§ 371 (c)(1),
(2) Date: May 17, 2022

(87) PCT Pub. No.: WO2021/099749
PCT Pub. Date: May 27, 2021

(65) Prior Publication Data
US 2022/0410145 A1      Dec. 29, 2022

(30) Foreign Application Priority Data
Nov. 19, 2019      (FR) ........................................ 1912912

(51) Int. Cl.
*B01L 3/00* (2006.01)
*G01N 33/487* (2006.01)
*G01N 33/49* (2006.01)
(52) U.S. Cl.
CPC ...... *B01L 3/5023* (2013.01); *G01N 33/48735* (2013.01); *G01N 33/491* (2013.01);
(Continued)
(58) Field of Classification Search
CPC ............ B01L 3/5023; B01L 2200/028; B01L 2300/0645; B01L 2300/0681;
(Continued)

(56) References Cited

U.S. PATENT DOCUMENTS 4,834,888 A      5/1989   Polaschegg
5,985,164 A  *  11/1999   Chu ................... B01D 67/0058
                                                        216/41
(Continued)

FOREIGN PATENT DOCUMENTS

CN            108795693            6/2018
DE        102014209193 A1      11/2015
(Continued)

OTHER PUBLICATIONS

Liu Ya Oping et al. "A high-throughput liquid biopsy for rapid rare cell separation from 17,18 large-volume samples" Lab on a Chip, vol. 19, No. 1, Dec. 5, 2018 (Dec. 5, 2018), pp. 68-78 DOI: 10.1039/C8LC01048J (Year: 2018).*
(Continued)

*Primary Examiner* — Jennifer Wecker
*Assistant Examiner* — Britney N. Washington
(74) *Attorney, Agent, or Firm* — Thomas I Horstemeyer, LLP

(57)                    ABSTRACT

The invention relates to a system for detecting at least one species present in a fluid, preferably for detecting at least
(Continued)

one circulating cell or aggregate of cells present in a human or animal biological fluid, and in particular circulating tumor cells (CTC) present in a blood fluid, the detection system comprising means (20) for filtering the fluid, the filtering means (20) comprising a filtering membrane (21), the filtrating membrane comprising at least one pore (22) designed to retain a species of a given type present in the fluid, the filtration means (20) further comprising at least one opening (23) designed to ensure, during operation within the fluid, the continuous circulation of the biological fluid, even when the at least one pore (22) is occupied.

25 Claims, 20 Drawing Sheets

(52) U.S. Cl.
CPC . *B01L 2200/028* (2013.01); *B01L 2300/0645* (2013.01); *B01L 2300/0681* (2013.01)

(58) Field of Classification Search
CPC ........ B01L 2200/143; G01N 33/48735; G01N 33/491; G01N 27/02
See application file for complete search history.

(56) References Cited

U.S. PATENT DOCUMENTS

| | | | |
|---|---|---|---|
| 2004/0053290 A1* | 3/2004 | Terbrueggen .... | G01N 35/00871 205/777.5 |
| 2011/0177551 A1 | 7/2011 | Mimitsuka | |
| 2014/0348706 A1* | 11/2014 | Rahman ............ | B01L 3/502761 422/502 |
| 2017/0189907 A1* | 7/2017 | Tibbe .................... | B01L 3/5085 |

FOREIGN PATENT DOCUMENTS

| | | | |
|---|---|---|---|
| JP | 2012065649 A | 4/2012 | |
| WO | WO-2015172992 A1 * | 11/2015 | ....... G01N 33/48735 |
| WO | 2016140183 A1 | 9/2016 | |

OTHER PUBLICATIONS

Alejandro Kayum Jimenez Zenteno. "Engineered micro-devices for the isolation of circulating 1,9-16,19-21 tumor cells in clinical routine" Sep. 21, 2018 (Sep. 21, 2018), Retrieved from the Internet: https://hal.laas.fr/tel-02137588/document (Year: 2018).*

Liu Ya Oping et al. "A high-throughput liquid biopsy for rapid rare cell separation from 17,18 large-volume samples" Lab on a Chip, vol. 19, No. 1, Dec. 5, 2018 (Dec. 5, 2018), pp. 68-78 DOI: 10.1039/C8LC01048J ISSN: 1473-0197, XP055781250 (Year: 2018).*

Japanese Office Action in related JP Application No. JP2022-554965, mailed Jul. 30, 2024 (with English Translation).

Liu et al., A high-throughput liquid biopsy for rapid rare cell separation from large-volume samples, Lab Chip, Dec. 5, 2018, vol. 19, p. 68-78.

Alejandro Kayum Jimenez Zenteno: "Engineered micro-devices for the isolation of circulating tumor cells in clinical routine", Sep. 21, 2018 (Sep. 21, 2018), XP055729508, Extra it de l 'Internet: URL:https:// hal.laas.fr/tel-02137588/document [extrait le Sep. 10, 2020] * p. 124-p. 130; figures 3.13, 3.18-3.21; tableau 2.1.

Liu Yaoping et al: A high-throughput liquid biopsy for rapid rare cell separation from large-volume samples11 , Lab on a Chip, vol. 19, No. 1, Dec. 5, 2018 (Dec. 5, 2018), pp. 68-78, XP055781250, ISSN: 1473-0197, DOI: 10.1039/C8LC01048J figure 3.

French Preliminary Search Report issued in FR 1912912, mailed Sep. 17, 2020.

International Search Report issued in PCT/FR2020/052138, mailed Mar. 12, 2021.

* cited by examiner

FIG. 9a
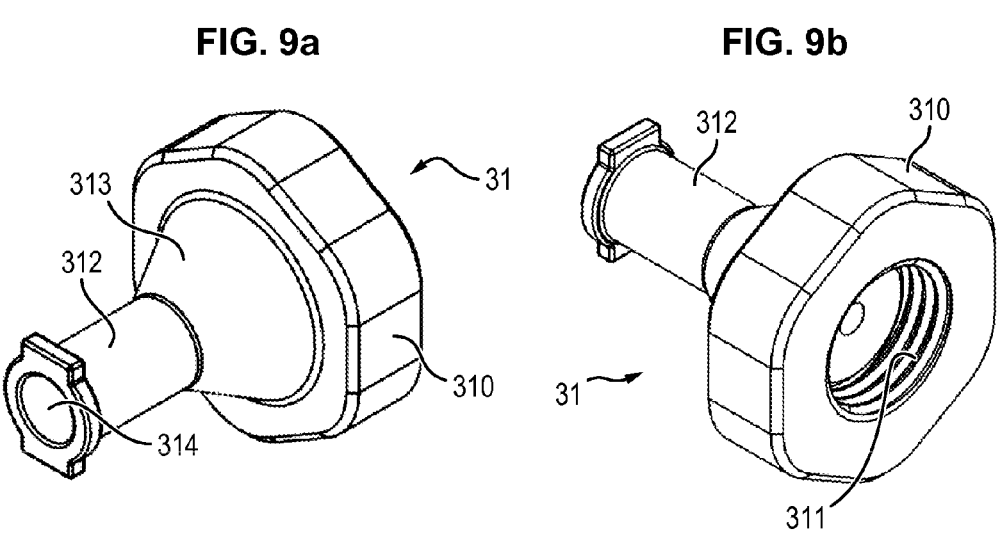
FIG. 9b
FIG. 9c
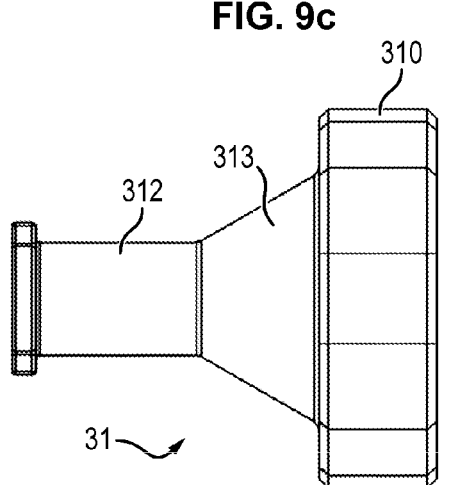
FIG. 9d
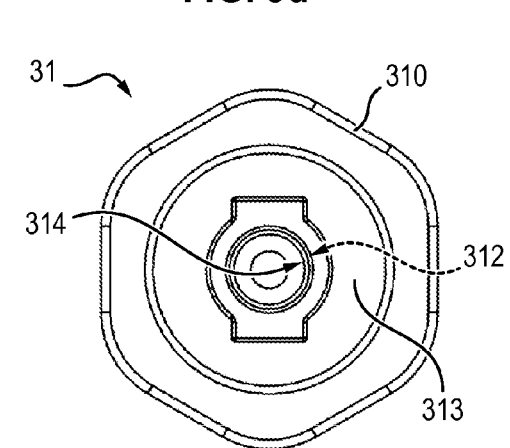
FIG. 9e
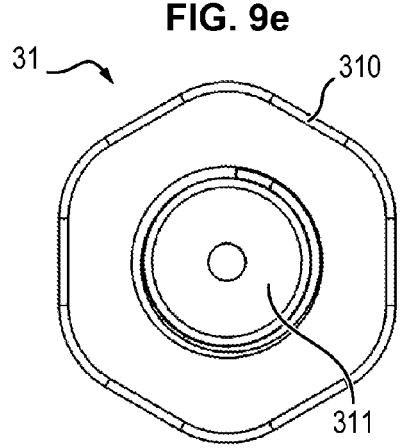

330

33

332

331

33

331

33

SYSTEM FOR CAPTURING AND DETECTING SPECIES PRESENT IN A BIOLOGICAL FLUID

CROSS REFERENCE TO RELATED APPLICATIONS

This application is the 35 U.S.C. § 371 national stage application of PCT Application No. PCT/FR2020/052138, filed Nov. 19, 2020, which application claims the benefit of French Application No. FR 1912912 filed Nov. 19, 2019, both of which are hereby incorporated by reference herein in their entireties.

GENERAL TECHNICAL FIELD

The invention relates to the field of capturing specific species or particles present in a biological or non-biological fluid (blood and its derivatives such as plasma and serum, urine, water, air, and any other fluid requiring analysis). The invention relates in particular to the capture of cells of interest present in a biological fluid such as blood in order to analyze these cells for medical monitoring. The invention is particularly applicable to the detection of circulating tumor cells for the medical monitoring of a patient suffering from a cancerous pathology and/or the almost complete extraction of tumor cells contained in the blood, for the diagnosis of a cancerous pathology, and for oncological therapy, the invention allowing to filter/extract tumor cells. The invention also applies to prognosis and monitoring of therapeutic efficacy by means of the detectable cells.

STATE OF THE ART

A fluid may carry several types of species or beads that are of interest to enumerate and analyze. In particular, animal or human biological fluids carry several types of cells, the presence of which may allow the monitoring or detection of different pathologies.

In particular, the circulating tumor cells (CTCs hereinafter) in the circulating blood are studied to help diagnose cancers and thus enable better treatment of patients.

In fact, the cancerous tumors release CTCs into the bloodstream and it has been shown that this phenomenon appears at an early stage of the disease. The biological and molecular analysis of one or more cell(s) allows a precise diagnosis and provides information on the aggressiveness of the cancer and the effectiveness of a treatment. CTCs are therefore a biomarker of interest at all stages of cancer management, diagnosis, prognosis, and monitoring.

However, CTCs are present in extremely low concentrations in the blood of cancer patients (about $1/10^9$ normal blood cells). The isolation and/or near-complete extraction of these rare cells is therefore extremely difficult.

Various in vitro methods are known to carry out this isolation, based on immunodetection. They are based on the presence of EpCAM (epithelial cell adhesion molecule), a membrane antigen specific to cells of epithelial origin, on the surface of CTCs. A 7.5 ml sample of blood is centrifuged and then placed in the presence of ferromagnetic nanoparticles with anti-EpCAM antibodies on their surface. The CTCs are then separated from the other cells by applying a magnetic field.

Two disadvantages are associated with this system:

a very limited blood sample is used (7.5 ml which corresponds to 0.15% of the total blood volume), in which the number of CTCs, given their low concentration, is very low;

it does not allow the detection of CTCs that have lost the EpCAM protein during the epithelial-mesenchymal transition (EMT), which represents about ⅔ of the total population of these cells; on the other hand, it only allows the detection of differentiated cells that have a limited life cycle and are not the most dangerous.

Other approaches to isolate CTCs in vitro from a blood sample are known, based on the size of the CTCs. In particular, the ISET system ("Isolation by Size of Epithelial Tumor Cells") uses the filtration of a treated blood sample (prior lysis of red blood cells) on a microperforated polycarbonate membrane; in this system, the CTCs are previously rigidified by application of paraformaldehyde so as to withstand the high pressure that is applied.

In general, the sensitivity of in vitro detection is reduced by the small volume of the samples. Indeed, given the rarity of CTCs in the blood, their presence in a sample of a few milliliters can amount to a few units at an already advanced stage of the cancer. Their detection at much earlier stages is therefore almost impossible.

More recently, systems designed for use in vivo or by apheresis have been developed to capture CTCs in the physiological medium, thereby preserving their viability as much as possible and potentially accessing larger blood volumes than those analyzed by in vitro systems.

Although the systems are more advantageous than the in vitro systems, none of the systems allow for the capture and the simultaneous enumeration of CTCs especially for real-time use.

Indeed, known systems use immunostaining techniques to identify the tumor nature of the captured cells. These techniques require post-capture manipulation, are expensive and do not allow direct real-time detection at the bedside. In addition, the platforms used must be transparent to allow the use of a fluorescence microscope to count the captured cells. Furthermore, these techniques do not guarantee the integrity of the labelled cells, which are altered before the biological analysis or their use in culture.

PRESENTATION OF THE INVENTION

The invention provides a system that overcomes the disadvantages of prior techniques.

To this end, the invention proposes, according to a first aspect, a system for detecting at least one species present in a fluid, preferably at least one circulating cell or cell aggregate present in a human or animal biological fluid, and in particular circulating tumor cells present in a blood fluid, the detection system comprising filtration means for said fluid, said filtration means comprising a filtering membrane, said filtering membrane comprising at least one pore adapted to retain a species of a given type present in the fluid, said filtration means further comprising at least one opening adapted to ensure, in operation within the fluid, a continuity of circulation of the biological fluid even when said at least one pore is occupied.

The invention according to the first aspect is advantageously completed by the following features, taken alone or in any technically possible combination thereof:

the system comprises a plurality of electrodes arranged around said at least one pore, said electrodes forming one or more electrical circuits polarized by an AC electrical signal allowing the measurement of complex impedance variations between these electrodes, as soon as one or more cells are housed in or near a pore, the measurement of the variation of the complex impedance modulus and its phase allowing to discriminate the type of cells;

the AC electrical signal applied to the electrodes has a frequency such that an electric field created by the electrodes enables the capture or release of cells in the pores by virtue of the dielectrophoretic force generated between the electrodes;

the polarization frequency induces a positive dielectrophoretic force during the capture so as to center the cells between the electrodes and to retain the cells in the pores;

the polarization frequency induces a negative dielectrophoretic force to detach all captured cells, the frequency being typically at 1 MHz;

the frequency induces a dielectrophoretic force to selectively detach a cell type, the frequency being between 50 KHz and 150 kHz, preferably at 100 kHz for detaching the tumor cells;

the polarization frequency is increased in steps between 10 KHz and 200 kHz in order to detach cells at different times depending on their dielectric properties;

the system further comprises an inductor connected to the electrodes so as to form an electromagnetic resonator circuit, the electrodes and inductor forming a circuit for detecting, preferably remotely searchable, the presence of trapped cells;

the filtering membrane is made of a material selected from the group comprising glass or metal (Nickel, Gold) or polymer, ferromagnetic material, magnetic material (NiFe), or the combination of glass and Silicon or Nickel and Silicon, Silicon Nitride, Silicon Oxide, Silicon or more generally a biocompatible and non-toxic material;

the pores have a cross-sectional dimension of between 0.1 μm and 100 μm, preferably between 8 μm and 12 μm or between 8 μm and 15 μm; and/or the pores are spaced at an interval of between 100 nm and 100 μm; the number of pores is between 100 and 100 000 000;

the pores are substantially circular or substantially oval or substantially polygonal or slit-shaped;

the pores of the membrane are arranged in groups of several pores, each group having a pattern, and the groups can be connected to each other via a row of pores;

the pattern formed by a group has a shape: hexagonal, circular;

the membrane comprises several groups of pores arranged in a square or star-shaped structure;

the pores of the membrane are randomly arranged;

the filtration means comprise a planar support comprising a recessed area in which the filtering membrane is located, and in which said opening is formed, said opening being arranged at the periphery of the filtering membrane;

the system comprises a compartment in which the filtration means are housed, the compartment comprising an inlet module and an outlet module joined together to allow fluid to flow from the inlet module to the outlet module passing through the filtration means;

the system comprises an inlet rack and an outlet rack, a blade supporting the filtration means, the inlet rack and the outlet rack being joined together so that the blade is between the inlet rack and the outlet rack to allow fluid to flow from the inlet rack to the outlet rack passing through the filtration means.

The invention according to the second aspect provides a capture assembly comprising a plurality of systems according to the invention disposed in series, each system comprising filtration means adapted to retain one type of species. The invention according to the second aspect is advantageously completed by the following features, taken alone or in any technically possible combination thereof:

the assembly comprises an inlet module, an outlet module, and at least one intermediate module arranged between the inlet module and the outlet module, the intermediate module and the outlet module supporting filtration means, said modules comprising means for fixing them together;

the inlet module comprises a fluid inlet and the outlet module comprises a fluid outlet;

the assembly comprises an input rack, an output rack, and at least one intermediate rack arranged between the input rack and the output rack, the intermediate rack and the output rack supporting filtration means, said racks comprising means for fixing them together to form a unitary assembly.

The invention also relates to a method for capturing cells circulating in a fluid, comprising a step of circulating a fluid in a system according to the first aspect of the invention, the method comprising a step of applying an electrical signal to electrodes having a frequency such that an electric field created by the electrodes enables captured cells to be captured or released from the pores by virtue of the dielectrophoretic force generated between the electrodes.

The method according to the invention is advantageously completed by the following features, taken alone or in any technically possible combination thereof:

the polarization frequency induces a positive dielectrophoretic force during the capture so as to center the cells between the electrodes and to retain the cells in the pores;

the polarization frequency induces a negative dielectrophoretic force to detach all the captured cells, the frequency being typically at 1 MHz;

the frequency induces a dielectrophoretic force to selectively detach a cell type, the frequency being between 50 KHz and 150 kHz, preferably 100 KHz for detaching tumor cells;

the polarization frequency is increased in steps between 10 KHz and 200 kHz in order to detach the captured cells at different times according to their dielectric properties.

The capture of different species is based on the physical properties of the species circulating in a fluid and in particular on their size and deformability. In the case of cells, the fluid is biological (blood, urine, lymph and in general any fluid circulating in a human or animal and carrying cells of interest to be analyzed). This biological fluid may or may not be diluted in a buffer solution. This fluid may also be a culture medium.

For cells potentially present in the blood, platelets are 2-4 μm in size and red blood cells are about 7 μm in size; white blood cells vary in size from 7 to 15 μm but are highly deformable. CTCs vary in size from 4 to 25 μm but are not very deformable.

Therefore, as long as the cells have low deformability, they can be captured by the filtration means while allowing other non-tumor components of the biological fluid to pass under normal blood flow conditions as existing in vivo.

The presence of the openings ensures a continuity of circulation of the biological fluid under in vivo conditions of pressure and velocity, whatever the filling of the filtering membrane with the captured elements.

Preferably, by coupling the filtering membrane and its ports to electrodes, the invention combines the physical capture with the detection of cells trapped in the vicinity of the pores. Thus, the enumeration of captured cells can be performed in real time.

In particular, when it comes to CTCs, these having specific dielectric properties, they influence the impedance of the electrical circuit formed by the electrodes. They influence an electrical signal in real time and therefore allow real time detection of the cells captured by the filtration means or the rate of obstruction of the filtration means. The detection of the rate of obstruction makes it possible to determine whether the filtration means can capture species without being saturated.

Based on the observation that CTCs have different dielectric properties from other cells that might be trapped, it is possible to discriminate them among the captured cells.

Real-time electrical detection of CTCs based on their dielectric properties makes it possible to avoid the steps of immunolabelling of tumor cells and the setting up of a system compatible with the optical microscopy necessary for the characterization of labelled cells. Thus, the invention makes it possible to directly characterize the presence of CTCs on the filtering membrane, avoiding the subsequent manipulation of the device. Medical information is therefore delivered instantly, at a lower cost and in a non-invasive manner. The real-time monitoring of the capture has a significant advantage for both in vivo and ex vivo uses by allowing the user to adjust the exposure time of the device to the blood fluid and tumor burden of the patient being analyzed, in order to tailor the exposure time of the device to the richness or sparsity of the information of the device and thus the accuracy of the medical information provided. In addition, the invention also allows the removal, after capture, of the circulating tumor cells contained in the blood providing a therapeutic modality.

The invention provides the clinician with immediate initial information on the number of species per unit of time or volume exposed, which can then be supplemented by analysis of the population thus captured. It should be noted that many analytical methods require minimal testing and that the invention also makes it possible to ensure that the conditions for carrying out the analyses are fulfilled before incurring often costly expenses. In addition, there is no need to collect, transport and prepare the sample. The quality of the information is preserved, the cells are isolated under native and physiological conditions, and this information is returned immediately to the specialist, at the place of consultation, for immediate decision-making. The invention also allows the generation of useful data for patient treatment. As blood fluid conditions vary from patient to patient and at the patient level throughout the day, this invention can be coupled with a local fluid velocity measurement to serve as a calibration or reference to build a comparable database.

Advantageously, thanks to the coupling of the electrical circuit formed by the electrodes to a resonator circuit, the impedance variations linked to the detection of the CTCs can be measured remotely and without contact in a remote wireless mode.

It is also possible to functionalize the surface of the system with antibodies and combine physical and affinity capture.

The release of the captured cells from the filtering device as a means of collection for analysis or re-culture can be achieved by electrical stimulation using the same electrodes used for detection.

PRESENTATION OF THE FIGURES

Additional features, purposes and advantages of the invention will be apparent from the following description, which is purely illustrative and non-limiting, and which should be read in conjunction with the attached drawings in which:

FIGS. 9a, 9b, 9c, 9d, 9e illustrate different views of an input module of a compartment of the system of the invention;

Figure 21:
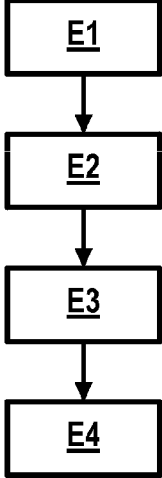

FIG. 21 schematically illustrates the steps of a capture and detection method according to the invention.

Throughout the figures, similar elements have identical references.

DETAILED DESCRIPTION

An embodiment of the invention is described below in the context of the capture and detection of cells present in a biological fluid, but the invention applies to the capture and detection of all types of species or beads present in a biological or non-biological fluid (blood and its derivatives such as plasma and serum, urine, water, air, pollutant, etc.)

It is specified that the invention applies to the capture of species and that species means: a tumor cell; an aggregate of tumor cells; a blood clot (the fluid being blood); an exosome.

Figure 1:
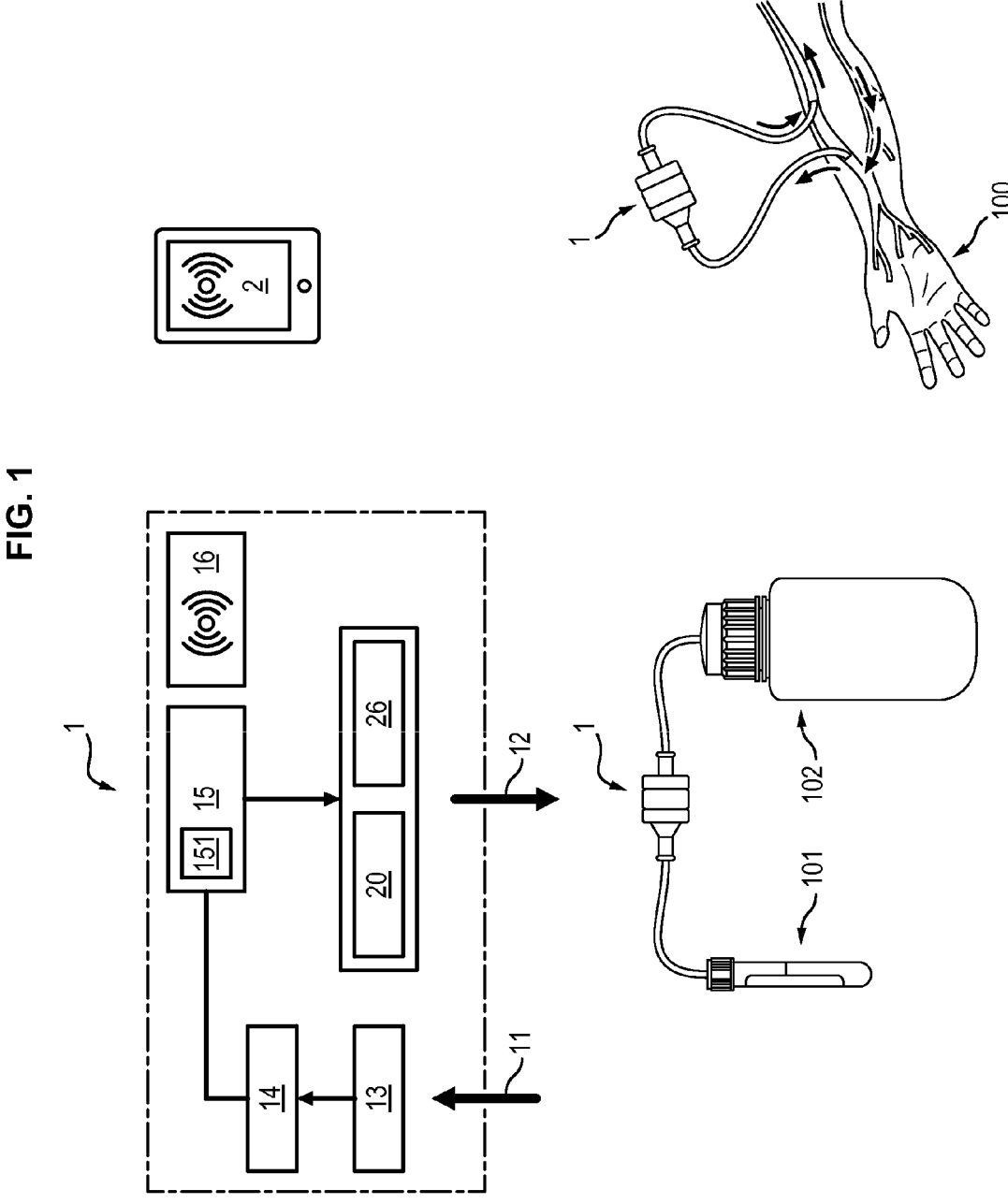
FIG. 1 illustrates a system for capturing species present in a fluid.

In relation to FIG. 1, a system 1 for capturing circulating cells present in a fluid comprises a fluid inlet 11 and a fluid outlet 12. It should be understood that a fluid is circulating and passing through the system described herein.

Such a system 1 may be connected to the bloodstream of a human via his/her arm 100 but it may of course also be connected to another part of the human or animal body. Preferably, the system will be connected to a peripheral vein (e.g. in the elbow crease) or to a central venous line of a human or animal. Alternatively, such a system 1 may be connected on the one hand to a test tube 101 containing a fluid and on the other hand to a system 102 for collecting the fluid after passing through the capture system 1.

In the case of ex vivo or in vitro use, a peristaltic or pressure-controlled pump 13 is connected to the fluid inlet, a flow sensor 14 allows the pump 13 to be regulated. The pump 13 is used to deliver the fluid to the filtration means 20 which will be described in detail below. Thus, the incoming fluid passes through the filtration means 20 and is re-injected into the patient's or animal's body or into a fluid collection tube. The fluid inlet and the fluid outlet are connected to the circulating fluid by means of catheters or by any other means known to the skilled in the art and adapted to the location where the system is to be used.

Alternatively, the system can be used in vivo and does not require a pump. In this case it is placed directly in the circulating fluid.

The filtration means 20 are advantageously coupled to a means 26 for detecting the captured cells.

A measurement unit 15 in connection with the detection means 26 measures information about the detected cells.

The system 1 also includes a wired or wireless communication interface 16 in communication with a wired or wireless terminal 2. Such a terminal 2 includes interfaces allowing a user to access various information relating to the detection.

Filtration Means

Figure 2:
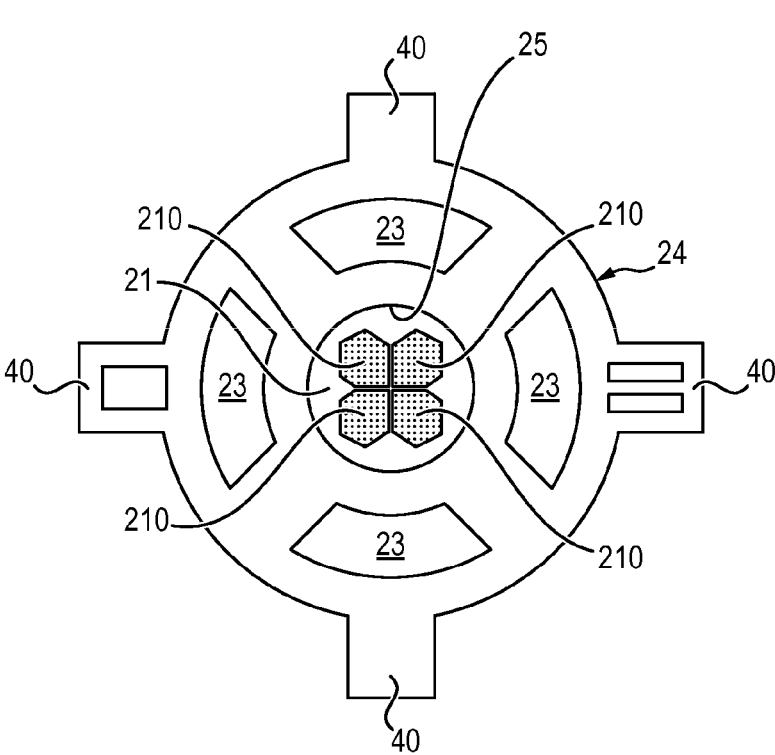
FIG. 2 illustrates a filtering membrane according to one embodiment of the invention.
Figure 3:
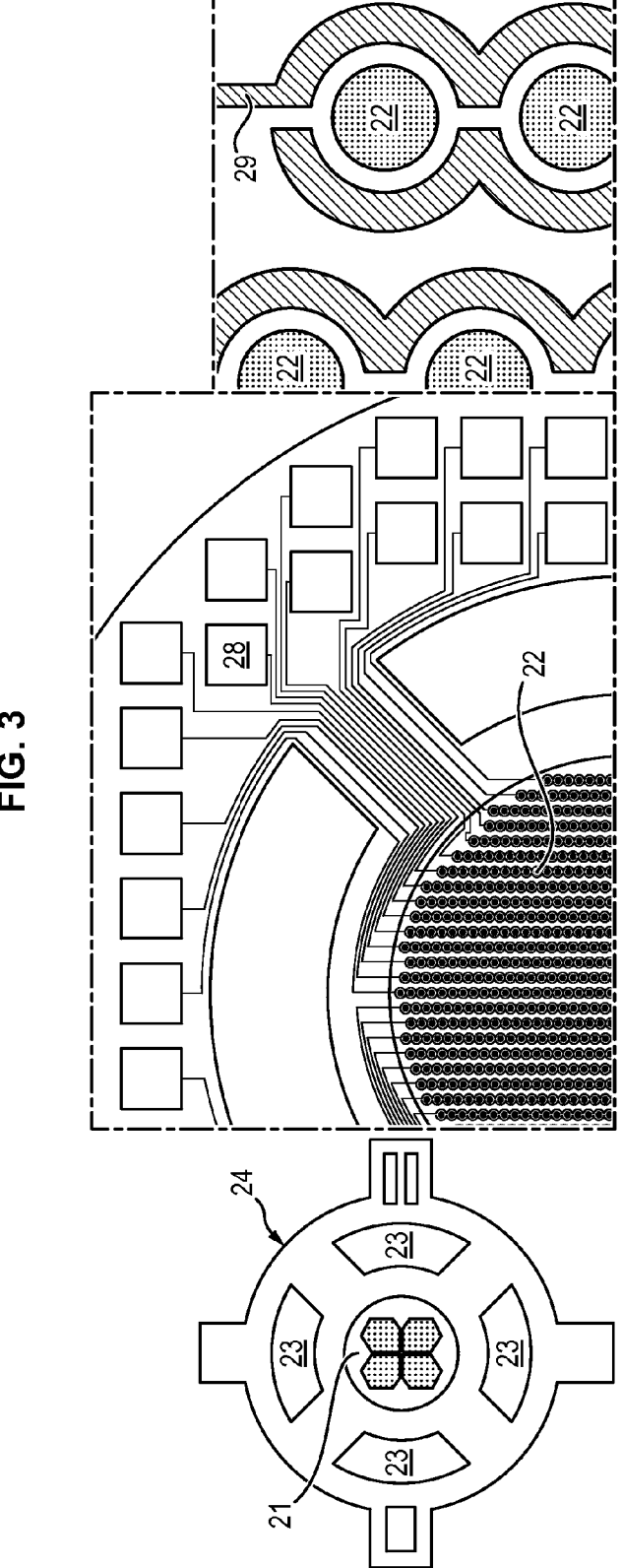
FIG. 3 illustrates a more detailed diagram of the membrane in FIG. 2.

FIGS. 2 and 3 illustrate a possible embodiment of the filtration means 20. This monolithic filtration means comprises a planar support 24, for example circular-shaped, comprising an area 25 in which a filtering membrane 21 is located.

The membrane is for example circular-shaped and is located in an area 25 of the same shape.

In the membrane are formed at least one pore 22 for capturing/retaining cells present in the biological fluid in which the filtration means 20 is placed. The fluid flows through the system.

The membrane consists of a biocompatible and non-toxic material selected from the group comprising glass or metal (Nickel, Gold), or polymer, ferromagnetic material, magnetic material (NiFe), multi-material (Glass/Silicon), Silicon Nitride, Silicon Oxide, Silicon.

Obviously, for applications where the fluid is not biological, the fact that the material is biocompatible is irrelevant.

The pores advantageously have a cross-sectional dimension of between 0.1 µm and 100 µm, preferably between 8 µm and 12 µm or between 8 µm and 15 µm and are typically in numbers of between 1000 and 6000, preferably between 100 and 100 000 000. The size and number of pores depend on the type of circulating cell to be captured and the way the filtration means are used (in vivo, ex vivo, in vitro).

Complementarily, the pores are spaced between 0.1 µm and 100 µm, preferably between 8 µm and 12 µm or between 8 µm and 15 µm.

The pores are of various shapes. They may be substantially circular or substantially oval or substantially polygonal or slit-shaped.

Advantageously, the pores of the membrane are arranged in groups of a plurality of pores, each group having a pattern, the groups being connectable to each other via a row of pores.

For example, in FIG. 2, the pores are arranged in four groups 210, each group having a polygonal shape.

Figure 4B:
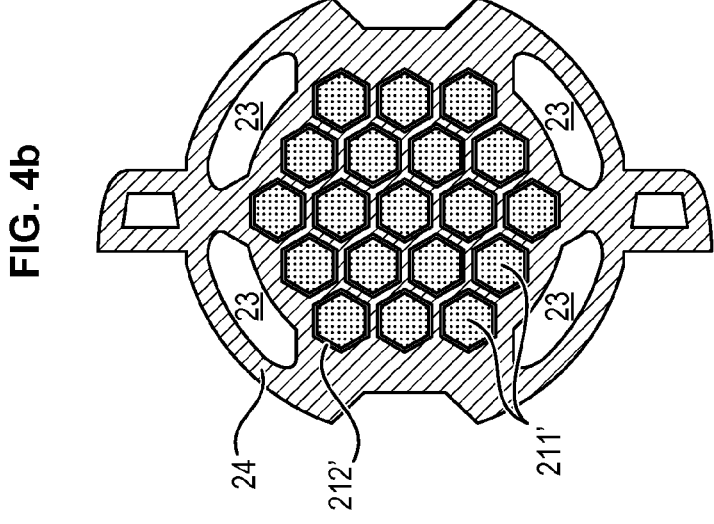
FIGS. 4a, 4b, 5 and 6 illustrate a diagram of the filtering membranes in different embodiments.
Figure 4A:
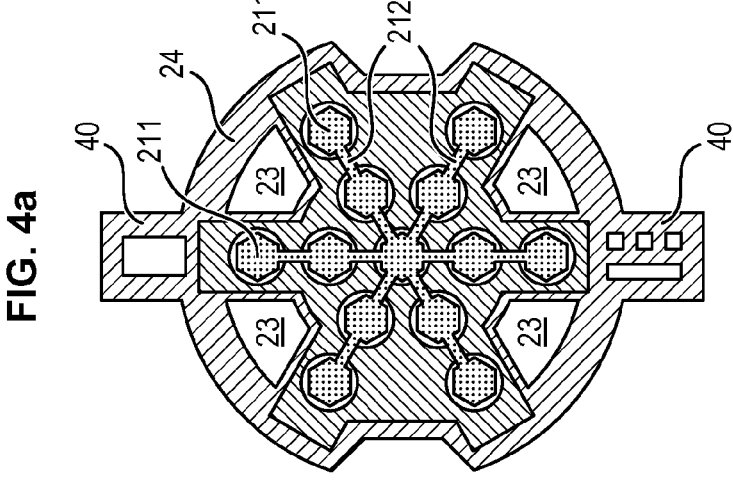

The groups can be placed on the membrane in several patterns: in square (FIG. 2) or in a star shape (FIG. 4a). As for the star structure the pores are arranged in hexagonal-shaped groups 211, the hexagonal-shaped groups 211 are connected to each other by groups 212 of slit-shaped pores. Thus, the star structure is obtained by combining two groups of pores. The star structure extends from a central group 211 placed in the center of the membrane and six branches extend from this central group. On each branch, two polygonal-shaped groups are connected to the central group, slots 212 connect the polygonal-shaped groups. The number of branches can of course vary as can the number of groups per branch.

Alternatively, as illustrated in relation to FIG. 4b, the pores arranged in groups 211' are not connected to each other but are in locations 212' independent of each other. This maximizes the number of pores on the support 24.

In order to allow continuity in the fluid flow, openings 23 are formed in the support at the periphery of the pores. In order to maintain an undisturbed blood flow, regardless of the degree of occultation of the filtering areas by the captured elements.

Referring again to FIGS. 2 and 3, the openings are shaped like an angular sector around the membrane. Such a shape is not limiting, and other shapes can be considered. Also, fluid disrupting or fluid concentrating elements can be arranged.

The number and shape of the openings are optimized to impair the mechanical strength of the filtration means 20 as little as possible. In the examples illustrated in FIGS. 2 and 3, four openings 23 are present while in the example illustrated in FIG. 5, six openings 23 are present.

Figure 6:
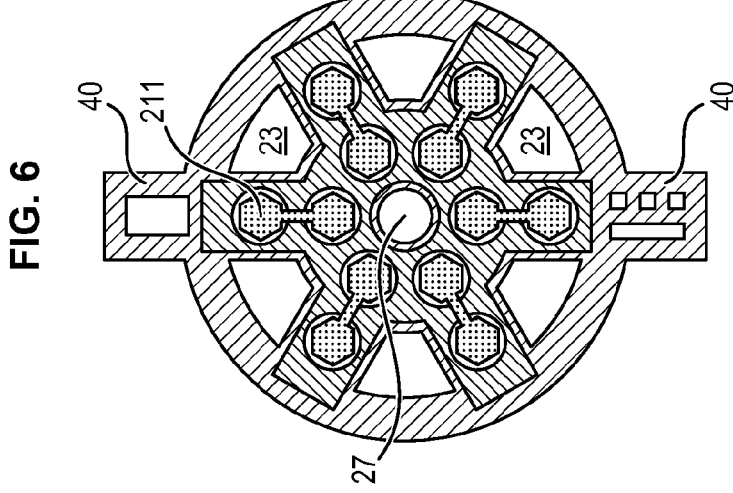

Alternatively, and in relation to FIG. 6, the membrane may comprise, in addition to the peripheral angular sector-shaped openings 23, a central opening 27. In this example, the pores are in polygonal-shaped groups connected in pairs by slit-shaped groups. The sets of two hexagonal groups are distributed in a star shape around the central opening 24.

For the configuration in FIG. 4, the following parameters can be used:

Diameter of circular pores 8 µm, 9 µm, 10 µm, 11 µm, 12 µm;

Inter-pore distance of 5 µm;

Number of pores: 4246, 3395, 2717, 2287, 1880;

Average number of pores per hexagonal group: 271, 220, 169, 135, 121;

Average number of pores per slit: 54, 45, 40, 27;

Surface area occupied by pores: 0.213 mm$^2$, 0.216 mm$^2$, 0.217 mm$^2$;

Total surface area of one opening: 0.111 mm$^2$;

Total area occupied by the four openings: 0.444 mm$^2$.

Figure 5:
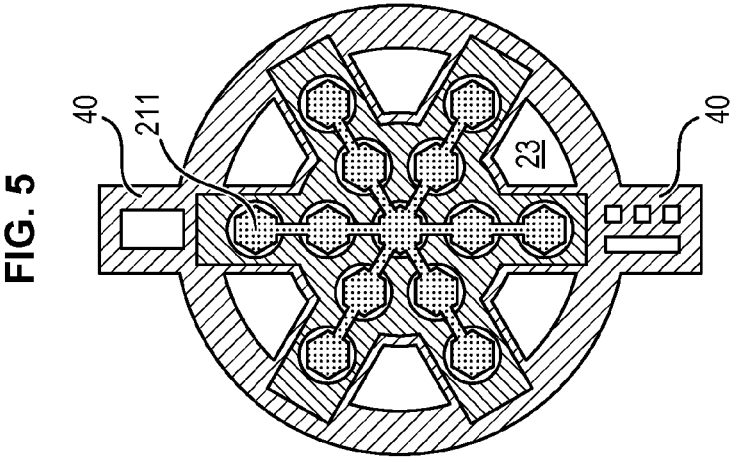

For the configuration in FIG. 5, the following parameters can be used:

Diameter of circular pores 8 µm, 9 µm, 10 µm, 11 µm, 12 µm;

Inter-port distance of 5 µm;

Number of pores: 3395, 4246, 2717, 2287, 1880;

Average number of pores per hexagonal group: 220, 271, 121, 169, 135;

Average number of pores per slit: 45, 54, 40, 27, 54;

Surface area occupied by pores: 0.216 mm$^2$, 0.213 mm$^2$, 0.217 mm$^2$;

Surface area of one opening: 0.111 mm$^2$

Total surface area occupied by the six openings: 0.666 mm$^2$.

For the configuration in FIG. 6, the following parameters can be used:

Pore diameter 8 μm, 9 μm, 10 μm, 11 μm, 12 μm;

Inter-pore distance of 5 μm;

Number of pores: 1227, 486, 386, 324, 271;

Average number of pores per hexagonal group: 220, 169, 135, 121;

Average number of pores per slit: 45, 40, 27;

Surface area occupied by the pores: 0.213 mm², 0.216 mm², 0.217 mm²;

Surface area occupied by the central opening: 0.057 mm²;

Surface area of one peripheral opening: 0.111 mm²;

Total surface area occupied by the six openings and the central opening: 0.723 mm².

Capture and Detection and Unit of Measurement

Figure 7:
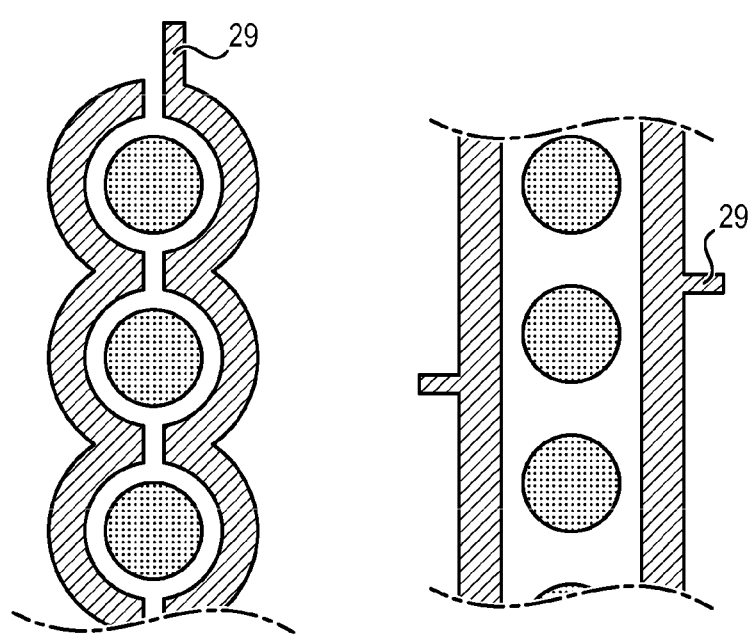
FIG. 7 illustrates two embodiments for the arrangement of the electrodes around the ports of the filtering membranes according to the invention.

In relation to FIGS. 3 and 7 and in order to detect the cells captured by the pores, using the filtration means 20, the capture and detection system advantageously comprises detection means 26 constituted by electrodes arranged around the pores 22. The electrodes 26 are connected together to form one or more electrical circuits characterized by a complex impedance which depends on the frequency of the electrical excitation. The value of this impedance depending on the frequency is influenced by the presence of cells in the vicinity of the electrodes bypassing the pores 22.

In particular, an AC voltage is applied to the electrodes at a given frequency so that a complex impedance is measured between the electrodes. The real part of the measured impedance is characteristic of the electrical resistance of the medium occupying that space. As for the imaginary part, it reflects the dielectric properties of the medium, in particular its permittivity. During the electrical measurement we measure the modulus of the complex impedance and the phase shift of the electrical current with respect to the applied voltage. These two measurements probe both the real and the imaginary part of the electrical impedance.

When a cell is positioned between the electrodes, the measured electrical impedance (by its modulus and "phase") is modified. The real part of the impedance is modified as well as the imaginary part. We therefore measure these two changes which we reproduce by the variation of the impedance modulus and by the variation of the current/voltage phase shift.

The measurement of the complex impedance makes it possible to discriminate the cell type, in particular tumorous/non-tumorous. It is indeed the variation of the imaginary part that contains the most valuable information in order to perform this type of detection.

In particular, as CTCs have specific dielectric properties, they vary the value of this impedance in a way that is distinguishable from other potentially trapped cell types. Depending on the variation detected, it is possible to detect the cells captured and their type. The electrodes are for example in gold, copper, platinum, nickel, piezoelectric materials, conductive polymer. The impedance is measured in a range from 10 Hz to 1 MHz or even 5 MHz.

These electrodes therefore surround the pores of the filtering membrane in order to electrically probe the dielectric properties of the medium in the vicinity of the pores where the captured cells are trapped.

The imaginary part of the electrical impedance, in the above-mentioned signal frequency ranges, is dominated by the capacitance formed by the cell's plasma membrane. This lipid bilayer, rich in membrane proteins, is an excellent electrical insulator separating two conductive media, the intra-cellular medium (the cytoplasm) and the extra-cellular medium (the fluid to be analyzed containing the cells), thus forming a sort of electrical capacitor described by a capacitance, i.e. by an imaginary impedance of capacitive origin.

In the absence of a cell between the electrodes, this membrane capacitance is not present in the electrical circuit, but when a cell is positioned between the electrodes (in the region where the electric field emanating from the electrodes is present), this membrane capacitance appears in the circuit. This change leads to a variation in the imaginary part of the measured impedance. Of course, at the same time, the real part of the impedance is also modified. Thus, both parts (real and imaginary) of the impedance that are modified by the presence of the cell are measured during the capture. Tumor cells circulating in the blood have a very specific plasma membrane morphology, resulting in the existence of numerous protuberances that are absent in healthy cells. These protuberances considerably increase the surface area of the plasma membrane of tumor cells when compared to the plasma surface of healthy cells. The membrane capacitance of the cell thus behaves like a flat capacitor whose capacitance is proportional to the surface area of the opposing conductors. This explains why the membrane capacitance of tumor cells is much greater than the membrane capacitance of healthy cells. Thus, the implemented detection allows not only to detect the cells retained by the capture device, but also to predict the healthy or tumoral nature of each captured cell, thanks to the magnitude of the variation in the imaginary part of the electrical impedance.

As illustrated in FIG. 7, the electrodes can surround the pores in various ways: by wrapping the pores or by forming straight tracks around the pores. The choice of the electrode shape depends on the pore density. Alternatively, the electrodes can be located on the inner walls of the pores.

Connection tracks 29 connecting the electrodes to contact pads 28 are required for direct (active) measurements. The pads 28 are connected to a measurement unit 15 which allows direct measurement of the value of impedance variations induced by the presence of cells between the electrodes.

The measurement unit may comprise a coil connected to the electrodes to form an electromagnetic resonator for passive and wireless measurements (interrogation of the device and reception of the remote signal). A wireless terminal 2 can then measure the variation in impedance of the detection circuits without contact. The coil can also be included in the membrane, and the value of its inductance can then be measured remotely.

Alternatively, a wire connection between the electrodes and the measurement unit 15 is possible and allows the impedance values of the detection circuits to be read directly.

The terminal 2 can also be wired to the measurement unit 15.

Regardless of how the impedance variation is measured, the measurement is direct and in real time. It is therefore possible to determine the presence of cells on the surface of the membrane. This impedance variation induced by the presence of cells in the vicinity of the capture pores depends on the nature of the trapped cells, and its measurement therefore makes it possible to distinguish which of the trapped cells are tumorous. This measurement is non-invasive for the cells to be detected and does not affect their viability in any way.

Capture and Detachment

The detection system is advantageously based on the use of dielectrophoretic force which, in association with the pores, makes it possible to hold the cells but also to detach them selectively.

Indeed, a dielectric object such as cells, bathed in a medium where a non-uniform electric field exists (we then speak of a gradient of the modulus of the electric field) is subject to a force capable of setting it in motion because of its polarizability.

This force is the basis of the principle of dielectrophoresis. In the presence of a non-uniform AC electric field, the direction of this force with respect to the gradient of the square of the modulus of the electric field depends on the frequency of the AC field and the dielectric properties of the object. For an object of a given size and permittivity, depending on the field frequency, the dielectrophoretic force can be positive (the dielectric object moves towards the regions with the highest electric field modulus) or negative (the dielectric object moves towards the regions with the lowest electric field modulus).

As described above, during the cell capture, an AC voltage is applied to the electrodes in order to detect them in real time. The configuration of the electrodes in planar form therefore leads to the generation of a non-uniform AC field above the electrodes, facing the fluid to be analyzed.

The regions of high electric field are close to the pores of the capture device, the regions of low electric field are further into the fluid above the microelectrodes. These electrokinetic phenomena related to the dielectrophoretic force therefore indicate that cells arriving in the vicinity of the pores will be subjected to forces that can either direct them towards the capture pores (positive dielectrophoresis) or repel them (negative dielectrophoresis).

The frequency at which the dielectric force changes sign is called the cut-off frequency. A dielectric object, depending on its shape, size and dielectric properties (its relative permittivity) has its own cut-off frequency.

In the case of circulating blood cells, the cut-off frequency of healthy blood cells is around 150 kHz, whereas that of tumor line cells is significantly lower (50 kHz). This is again a result of the different dielectric properties of tumor cells linked to a high membrane capacitance in this frequency range. Thus, it appears that by polarizing the electrodes at an intermediate frequency between these two frequencies the cells of interest can be selectively directed preferentially in a preferred direction in space.

Therefore, it is possible to use the detection system in several configurations that allow for a combination of detection by measuring electrical impedance and the application of a force that can lead to either better anchoring of the cells on the microelectrodes or to their detachment.

For the capture, a fluid is considered to be flowing in one direction, while for the collection a fluid is flowing in a direction opposite to that of the capture.

The first configuration is the capture. During the capture, the choice of a polarization frequency inducing a positive dielectrophoretic force allows a better localization of the cells on the electrodes, thus facilitating their electrical detection. The cells retained by the pores are thus always located in the same way, leading to a very high reproducibility of the electrical impedance measurements. At this stage, however, it is important not to exert too much force which would retain all the cells passing through the pores.

The second configuration is the collection of the cells after capture. After the capture, the polarization voltage is increased (the gradient of the electric field modulus is higher), the dielectrophoretic force exerted is now much stronger, the frequency is adjusted to a high value (1 MHz) so as to detach all captured cells for collection by negative dielectrophoresis. During this electrical detachment a fluid flow (opposite to that of the capture) is applied to collect the detached cells in a reservoir. During this step the nature of the circulating fluid can be chosen to preserve the cell viability while maximizing the dielectrophoretic force of detachment.

The third configuration is the selective detachment of cells. After the capture, the polarization voltage is increased (the gradient of the electric field modulus is higher), the frequency is now adjusted so as to selectively detach a single cell type by positioning at an intermediate frequency between 50 KHz and 150 kHz. During this electrical detachment a fluid flow (opposite to that of the capture) is applied to collect the detached cells in a specific reservoir. During this step, the nature of the circulating fluid can be chosen to preserve the cell viability while maximizing the dielectrophoretic force of detachment. It is then possible to selectively and sequentially detach different cell types. At 100 kHz only tumor cells are detached and collected.

The fourth configuration is the detachment and classification of the cells. After the capture, the polarization voltage is increased (the gradient of the electric field modulus is higher), the frequency is now increased in steps between 10 KHz and 200 kHz in order to detach the cells at different times depending on their dielectric properties. During these electrical detachments a fluid flow (opposite to that of the capture) is applied to collect the sequentially detached cells. During this step, the nature of the circulating fluid can be chosen to preserve the cell viability while maximizing the dielectrophoretic force of detachment. The detached cells are collected in a channel whose cross-section allows the transit of only one cell at a time. The cells are then arranged in a row with a position that depends on their dielectrophoretic cut-off frequency and therefore on their dielectric properties. In this queue, the cells will therefore be ordered according to their membrane capacitance and thus the healthy cells will be at the end of the queue and the tumor cells at the other end (at the head of the queue) with all possible gradations between these two ends.

The fifth configuration is the collection of the lysate of interest. After the capture, the polarization voltage is strongly increased (the gradient of the electric field modulus is even higher), the dielectrophoretic force exerted is very intense, the frequency is adjusted to a low value (10 kHz) and a cell lysis occurs releasing the contents of the captured cells. During this cell lysis a fluid flow (opposite to that of the capture) is applied to collect the cell lysate in a reservoir.

Compartment of the First Type

Figure 8:
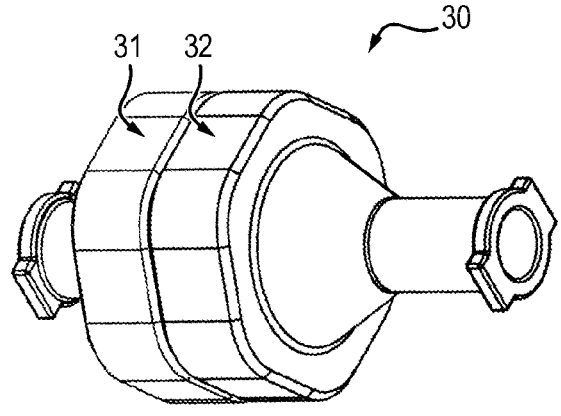
FIG. 8 illustrates a compartment of the system of the invention.
Figure 10A:
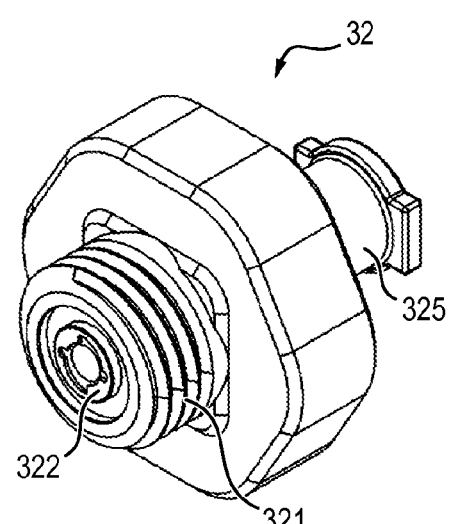
FIGS. 10a, 10b, 10c, 10d, 10e, 10f illustrate different views of an output module of a compartment of the system of the invention.
Figure 10B:
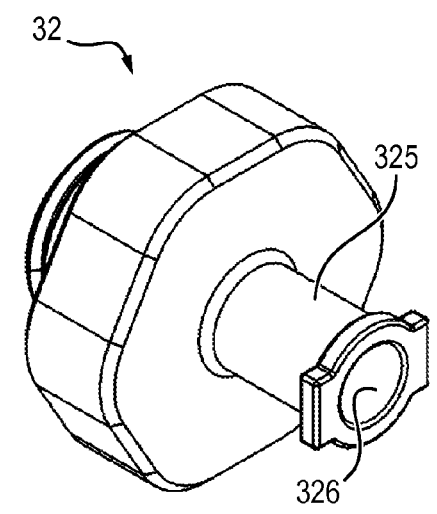
Figure 10C:
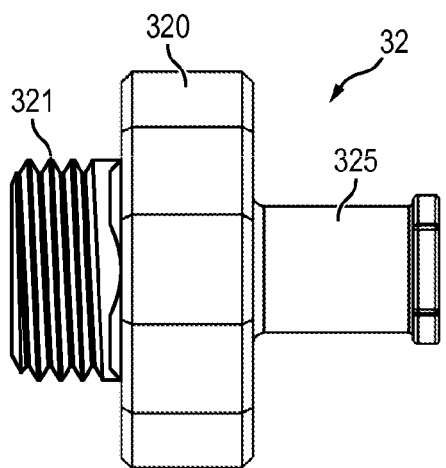
Figure 10D:
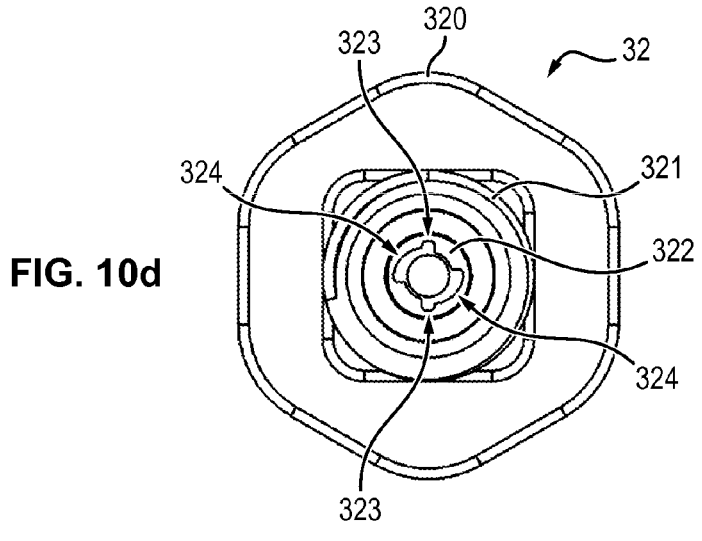
Figure 10E:
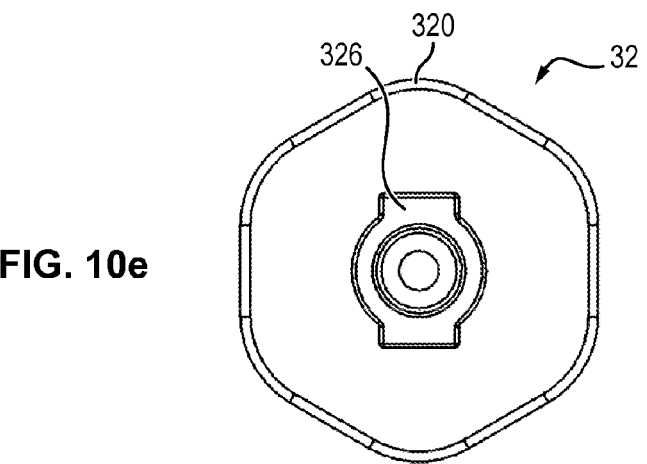
Figure 10F:
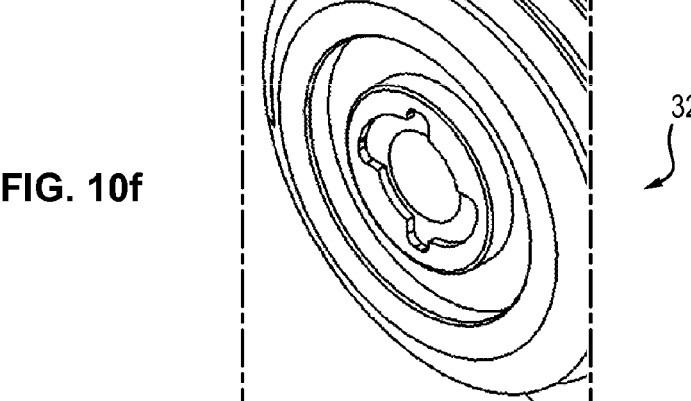

According to an embodiment, and as illustrated in FIG. 8, the capture and detection system advantageously comprises a compartment 30 in which the filtration means 20 are housed. This compartment comprises an inlet module 31 forming a female part and an outlet module 32 forming a male part 32. Thus, the inlet module and the outlet module can be assembled by screwing them together or by interlocking them.

The input module 31 is visible in FIGS. 9a, 9b, 9c, 9d and 9e and the output module 32 is visible in FIGS. 10a, 10b, 10c, 10d, 10e and 10f.

The input module 31 comprises a housing 311 forming the female part 310 for receiving the male part 321 of the output module 32. If the input module 31 and the output module 32 are screwed together, then the female part is tapped while the male part is threaded.

To feed fluid into the compartment, the inlet module 31 comprises a hollow rod 312 extended by a cone 313. The hollow rod 312 and the cone 313 are connected to the female part 310 and allow fluid to be fed from the inlet port 314 of the inlet module 31.

The inlet port 314 is shaped to be connected to a channel for supplying the fluid to be analyzed. The female part 310 has the shape of a hollow cylinder connected to the cone 313. The conical shape allows a large amount of flow at the inlet module.

Figure 11A:
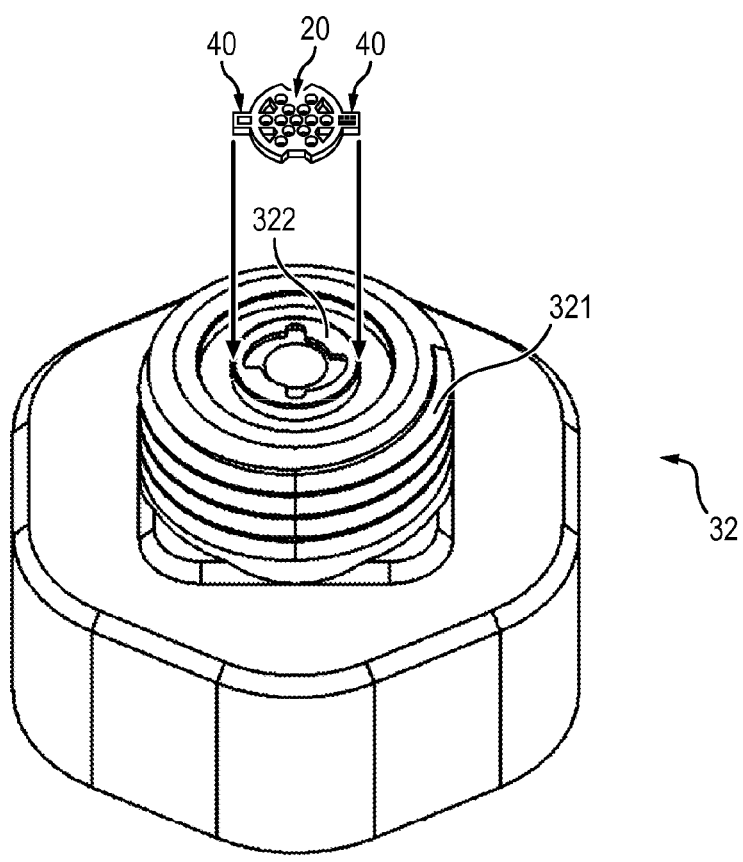
FIGS. 11a, 11b illustrate the attachment of a capture system in a compartment module of the system according to the invention.
Figure 11B:
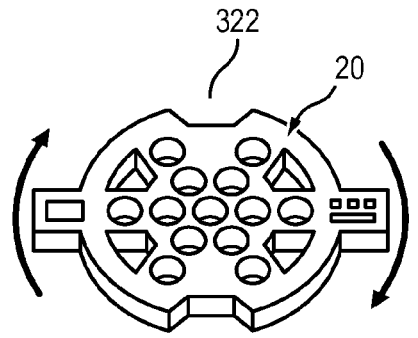

The male part 321 of the outlet module 32 comprises a slot 322 configured to receive the filtration means 20, which slot 322 is shaped to match the shape of the filtration means 20, which comprises tabs 40 (see FIG. 2) to allow them to be inserted and held in the slot 322. The filtration means 20 are inserted into the slot 322 by inserting the tabs into complementary housings 323 provided at the slot 322 and then by applying a rotation to the filtration means 20 these are brought into position to remain stationary. The slot 322 includes grooves 324 for insertion of the tabs to lock the filtration means in place after rotation. These grooves are machined on either side of the housings 323 receiving the tabs 40 of the filtration means 20. Electrical contacts may be provided in the grooves. FIGS. 11*a* and 11*b* illustrate the filtration means 20 arranged in the slot 322.

To allow fluid to exit the filtration means 20, the outlet module 32 comprises a hollow rod 325 connected to a hollow cylinder 320. The hollow cylinder 320 is between the male part 321 and the hollow rod 320. The hollow rod 325 has an outlet port 326 adapted to be connected to a channel for discharging the fluid after analysis.

When the inlet and outlet modules are assembled, the filtration means are inside the compartment and are not visible from the outside.

The advantage of the compartment is that it can be easily disassembled to replace the filtration means if necessary.

When the filtration means are arranged in the compartment, a one-piece unit is obtained.

The compartment is preferably made of a biocompatible material, especially when it is to be used in vivo.

Figure 12A:
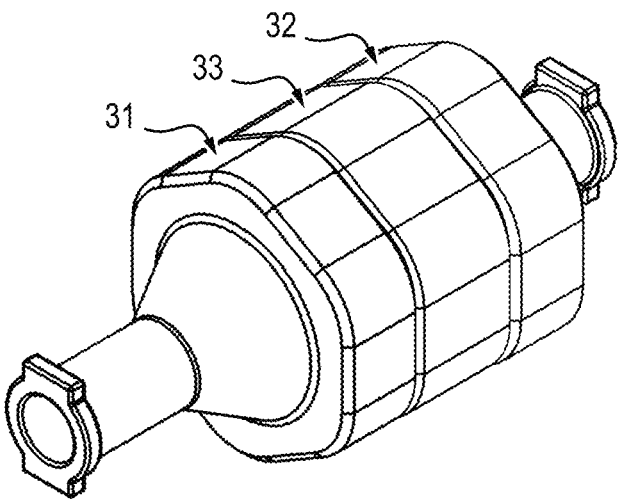
FIGS. 12a, 12b and 12c illustrate the compartment of FIG. 8 with an additional intermediate module.
Figure 12B:
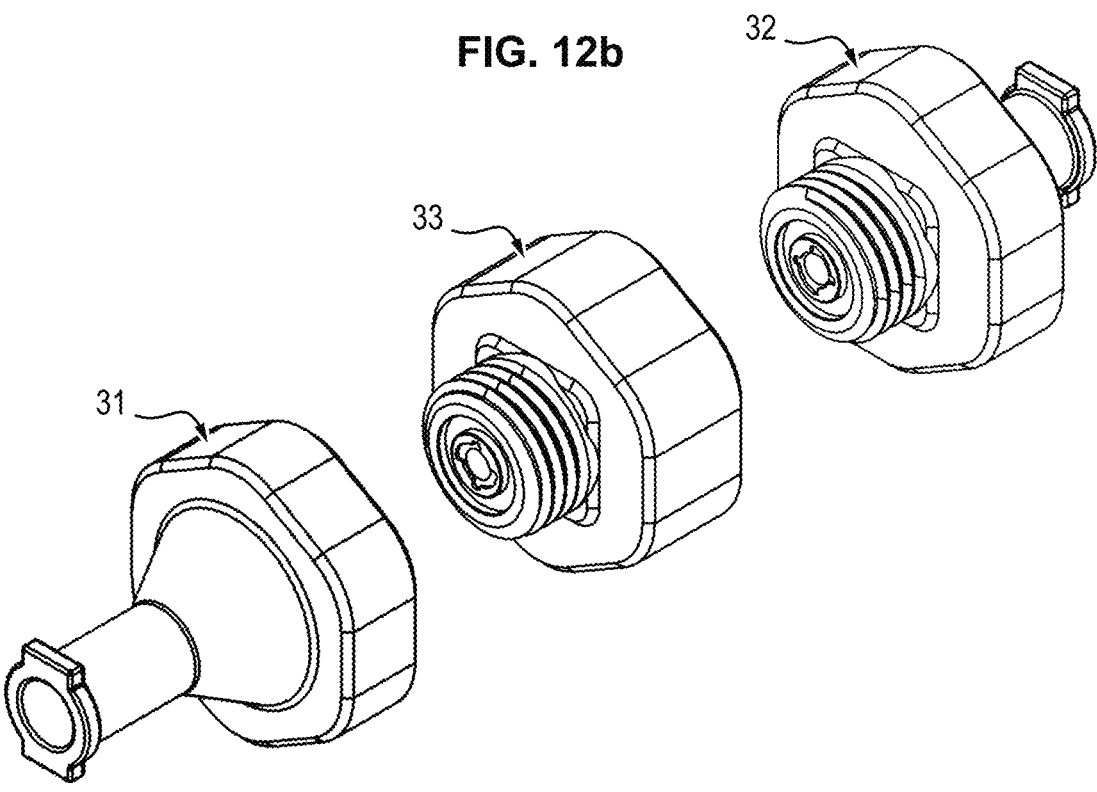
Figure 12C:
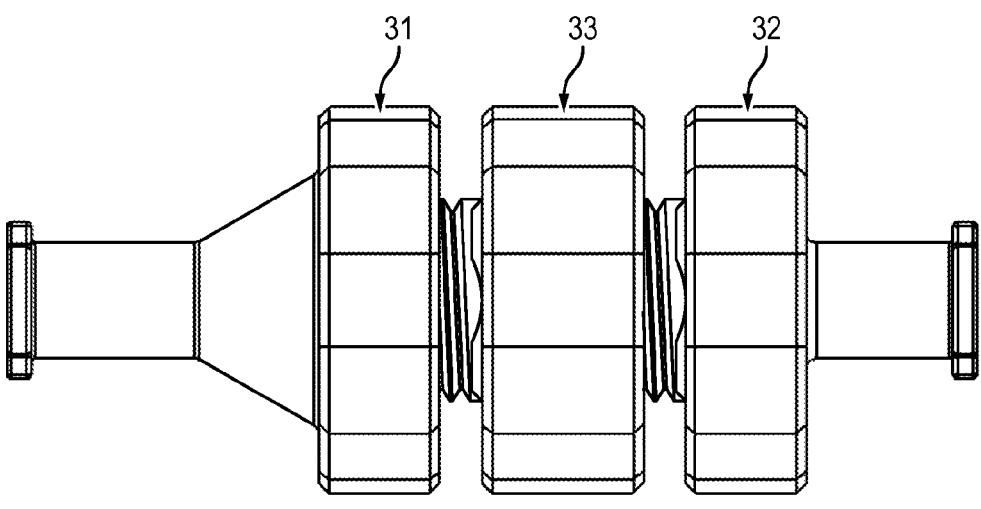
Figures 13A, 13B, 13C:
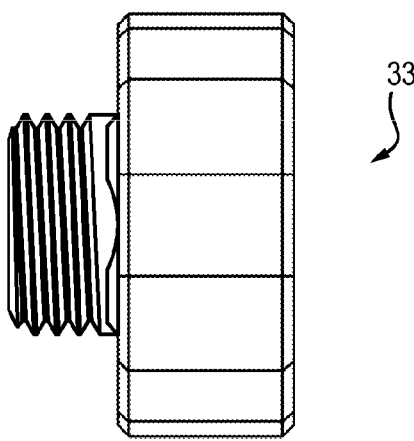
FIGS. 13a, 13b, 13c, 13d, 13e, 13f illustrate different views of an intermediate module of a compartment of the system of the invention.
Figure 13D:
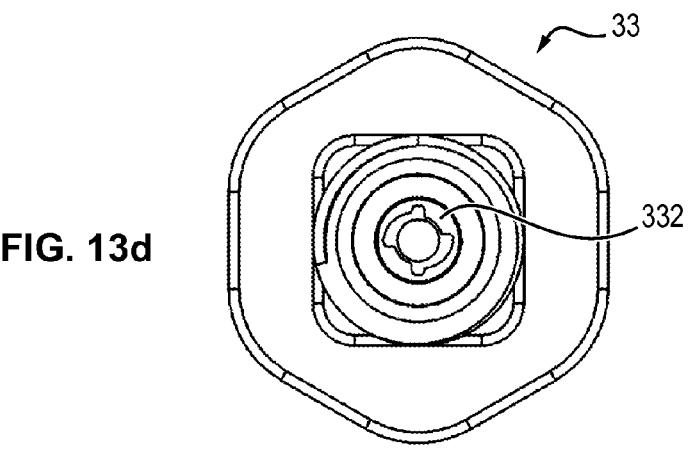
Figure 13E:
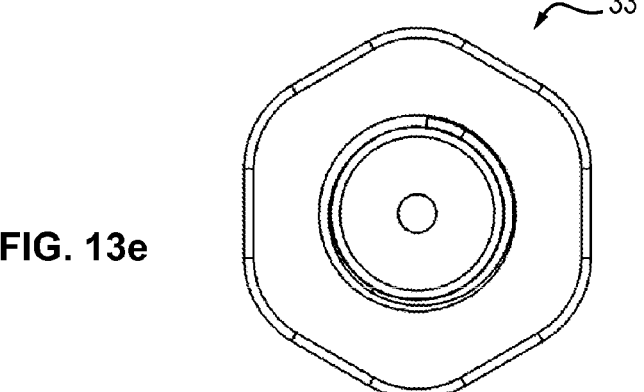
Figure 13F:
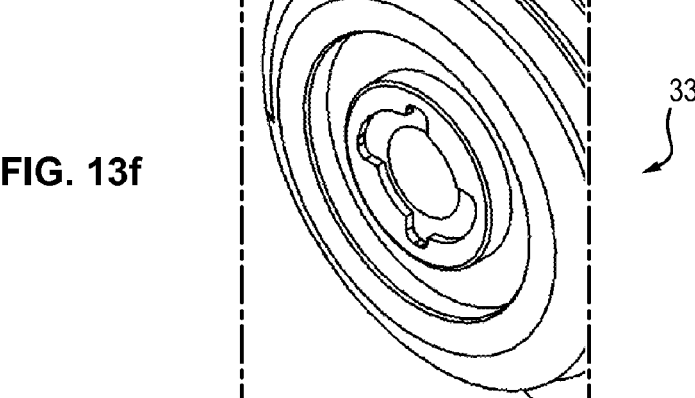
Figure 14:
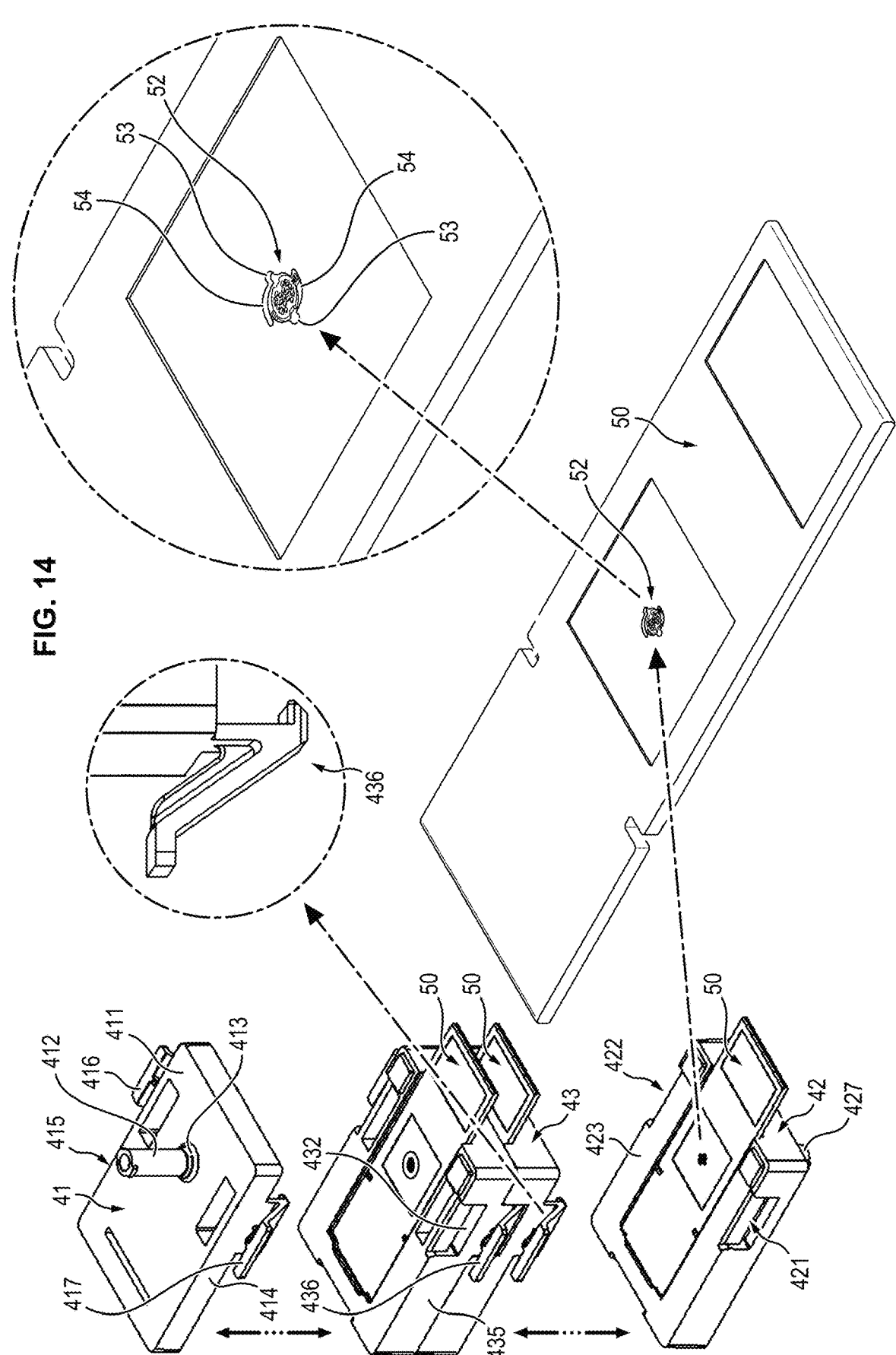
FIGS. 14 to 17 illustrate a rack and combinations of racks according to one embodiment of the invention.

According to one embodiment of the invention, as illustrated in FIGS. 12*a*, 12*b* and 12*c*, the filtration means may be arranged in series. Thus, there are a number of filtering membranes in series each having characteristics specific to the capture of one cell type. Alternatively, the membrane may be defined to capture more than one cell type. In this case, the membrane comprises pores of different sizes and shapes.

Series connection consists of assembling several modules together.

In FIG. 12*a*, from left to right, there is an input module 31 as described above, one or more intermediate modules 33 and an output module 32 as also described above.

The intermediate module can be seen in FIGS. 13*a*, 13*b*, 13*c*, 13*d*, 13*e* and 13*f*.

As can be seen in these figures, the intermediate module comprises a male part 331 and a female part 330. The intermediate module 33 may be screwed or plugged into/with the female part of the input module 31 and the male part of the output module 32 respectively. In the case where the intermediate module 33 is screwed in, it comprises a threaded male part and a trapped female part.

The male part 331 comprises a slot 332 for receiving a filtration means 20. The slot 332 has the same shape and characteristics as that of the outlet module 32 previously described.

In summary, the intermediate module 33 differs essentially from the output module in that it does not include a rod for the fluid outlet.

By installing one or more intermediate module(s), it is therefore possible to have several filtration means in series to capture and detect several types of cells.

Also, modules may be provided to allow the fluid to be modified as required. For example, a module can concentrate the fluid before it is filtered by the filtration means.

Thus, the result is a modular system that can be adapted to different cell types.

Compartment of the Second Type

According to an embodiment illustrated in FIGS. 14, 15, 16 and 17, the capture and detection system advantageously comprises an input rack 41 and an output rack 42 and possibly one or more intermediate rack(s) 43 arranged between the input rack 41 and the output rack 42 in order to connect in series several filtration means 40 as above.

The filtration means 20 are housed in the output rack 42 and, if necessary, in the intermediate racks 43.

Figure 15:
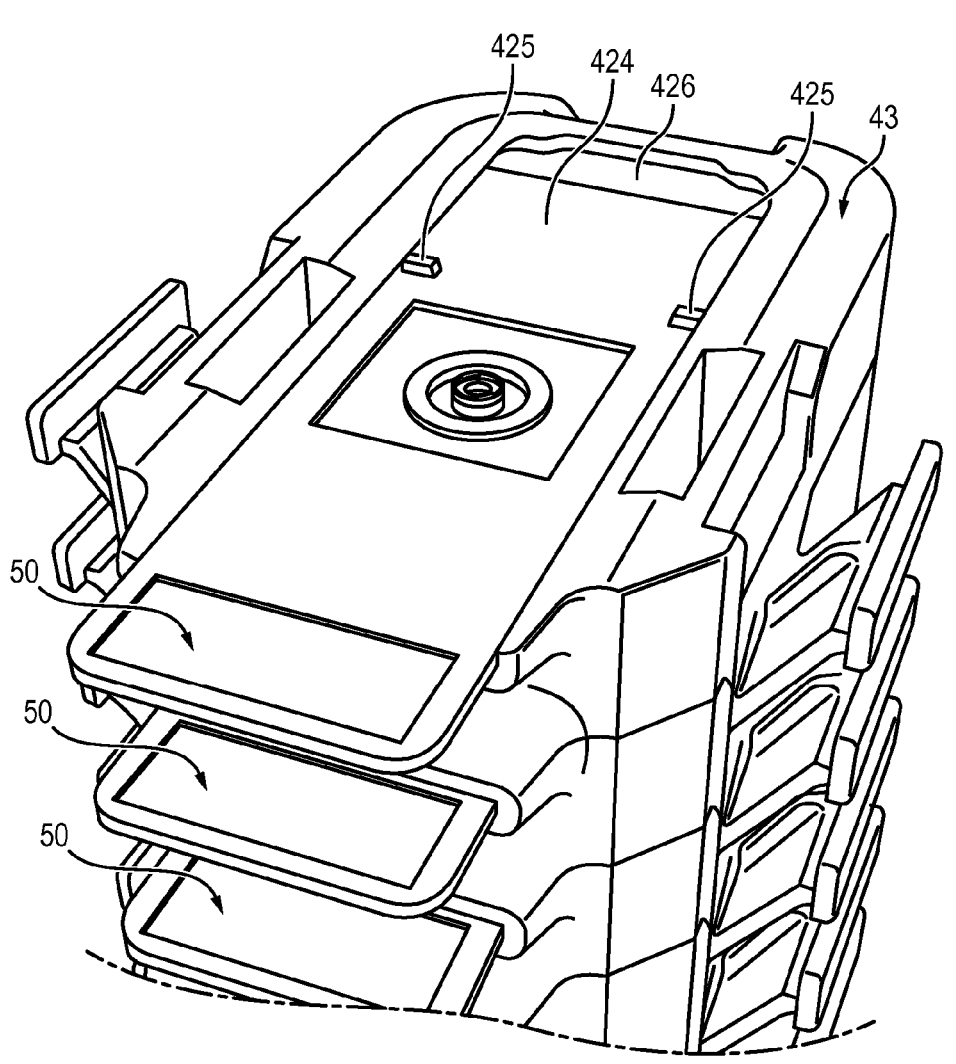

The racks 41, 42, 43 are such that they can fit together to form a stack of racks (see FIG. 15).

The inlet rack 41 is parallelepipedic and has a top face 411 comprising a hollow rod 412 which extends from a port 413. This allows the fluid to be fed in for analysis. This inlet rack 41 connects to the outlet rack 42 or to an intermediate rack 43. The input rack 41 comprises flexible tabs 416, 417 on its side faces 414, 415 which allow the input rack 41 to be clipped into complementary housings 421, 422, 431, 432 of the output rack 42 or the intermediate rack 43 to which it is connected.

The input rack 41 clips to the intermediate rack 43 or the output rack 41 so that the bottom surface 418 of the input rack rests on the top surface 423, 433 of the intermediate or output rack.

Figure 16:
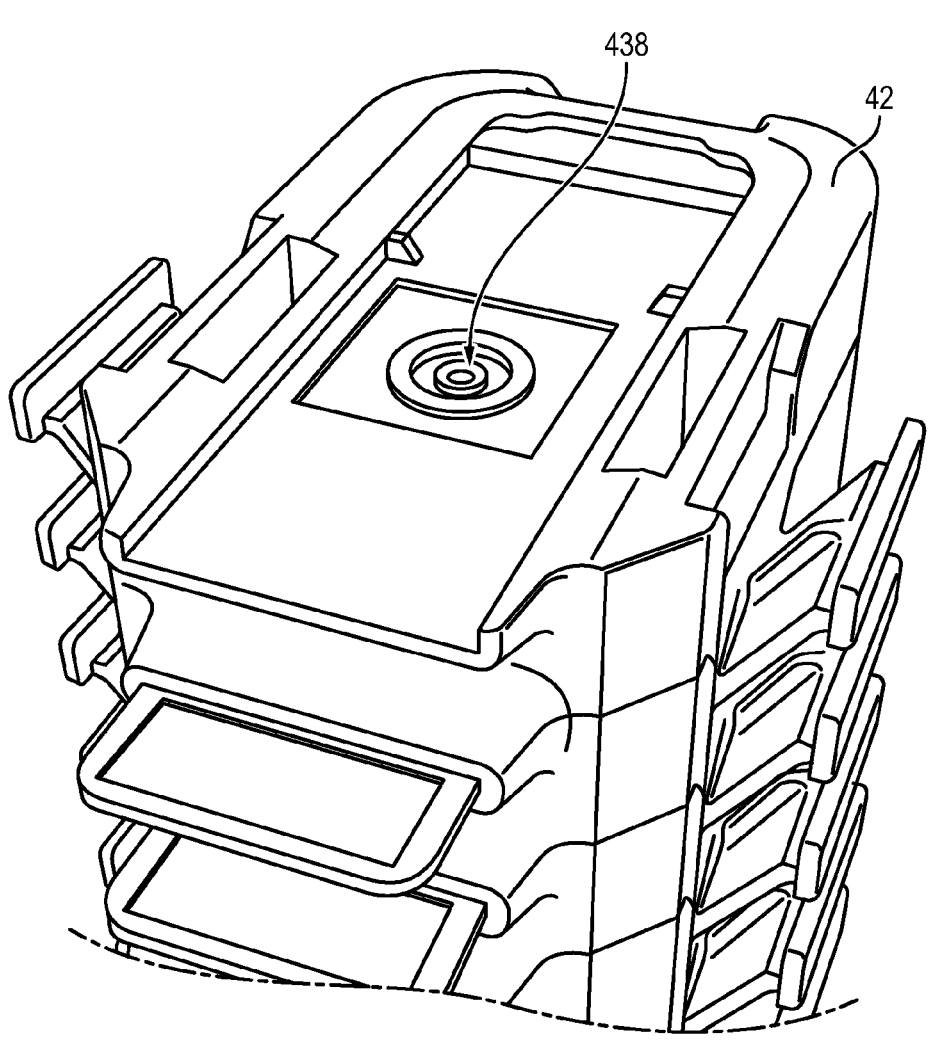
Figure 17:
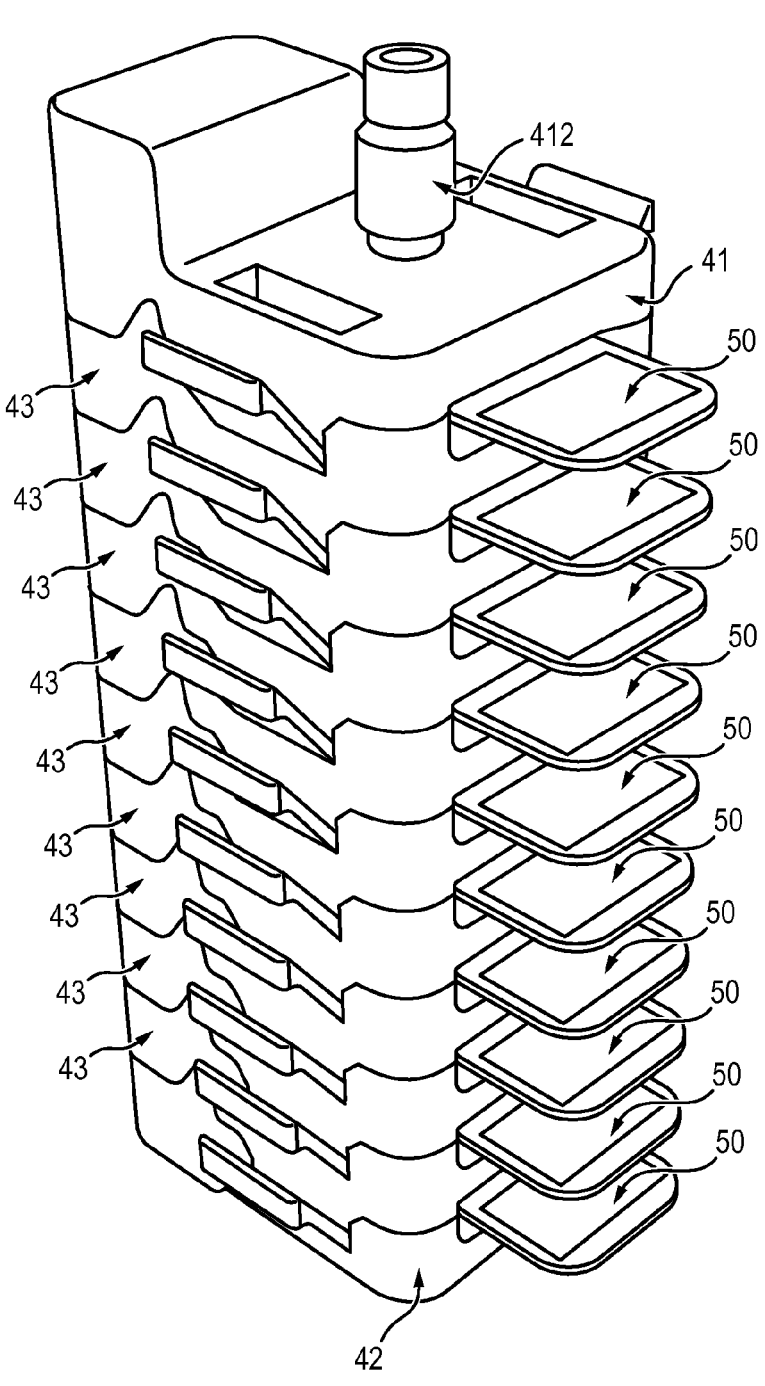

The output rack 42 is parallelepipedic and comprises on its upper face 423 a groove 424 forming a housing for a blade 50 of the type used for microscopes for example (see FIG. 16).

The housing 424 comprises two lugs 425 located opposite each other which enable the blade 50 to be held in position. In this respect, the blade 50, which is in the form of a plate, has slots 52 complementary to the lugs 425. The blade 50 is inserted into the housing 424 by resting on a reception space 426 formed at the bottom of the housing 424. The blade 50 is then lowered to rest in the housing 424. The outlet rack 42 has a port located on its lower face 427 located in its center for example to let the fluid to be analyzed pass through. The port is extended by a rod 428 similar to that used with the inlet rack 41. This rod can be connected to a channel which allows the fluid to be evacuated after passing through filtration means 20.

The intermediate rack 43 is parallelepipedic and comprises on its upper face 433 a groove 434 forming a housing for a blade 50 of the type used for microscopes for example (see FIG. 16). The top face of the intermediate rack 43 is similar to that of the output rack 42. As the intermediate rack 43 is intended to be arranged between two racks, the lower face of the intermediate rack comprises flexible tabs 436, 437 on its side faces 435 which allow it to be clipped into complementary housings 421, 432 of the rack to which it should be connected. The intermediate rack 43 includes a central port 438 to allow the fluid to pass through.

When several racks are stacked, the fluid to be analyzed circulates in several racks and therefore passes through several filtration means 20 supported by the blade 50 specific to each rack. The blade 50 has a slot 52 which has a shape adapted to the shape of the filtration means 20, which include tabs 40 (see FIG. 2) allowing them to be inserted and held in the slot. The filtration means 20 are inserted into the slot 52 by inserting the tabs into complementary housings 53 provided at the slot 52 and then by applying a rotation to the filtration means 20 the latter are set to remain stationary. The slot 52 includes grooves 54 where the tabs are inserted to lock the filtration means 20 in place after rotation. These grooves are machined on either side of the slots 52 receiving the tabs 40 of the filtration means 20. Electrical contacts may be provided in the grooves.

The advantage of the second type of compartment is that it allows the blade 50 to be easily removed from the racks.

Furthermore, as already mentioned, the use of at least one intermediate rack in addition to the output rack makes it possible to have multiple filtering membranes in series, each with specific characteristics for capturing one cell type. Alternatively, the membrane can be defined to capture multiple cell types. In this case, the membrane comprises pores of different sizes and shapes.

The racks described here are parallelepipedic but can take other shapes: cylindrical in particular.

Compartment of the Third Type

Figure 19:
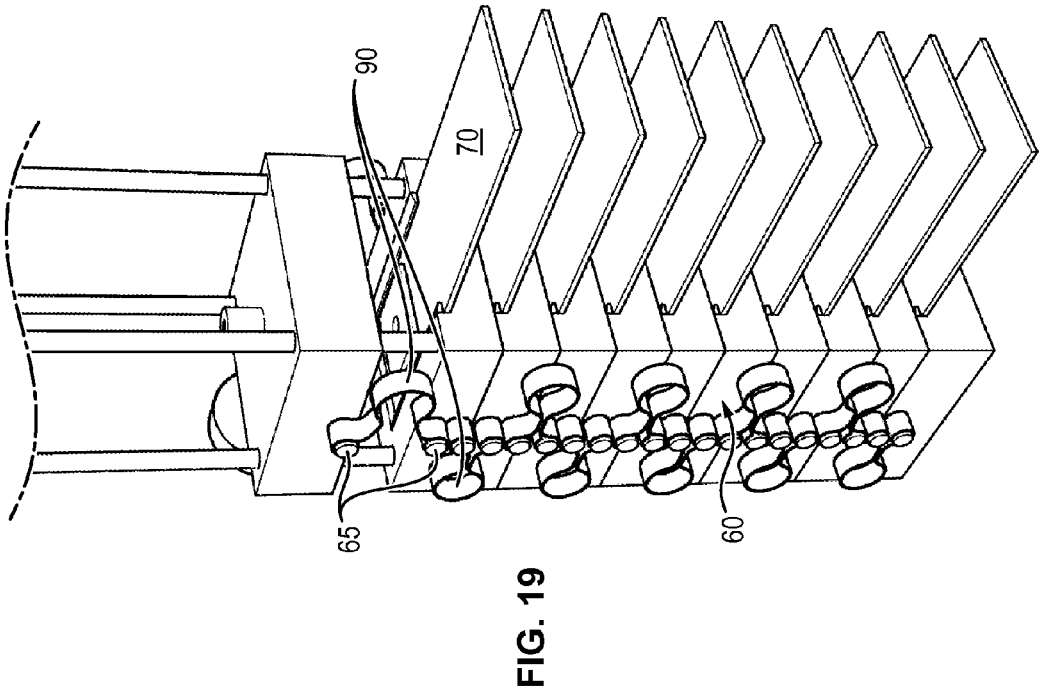
FIGS. 18 to 20 illustrate racks assembled together according to an embodiment of the invention.
Figure 18:
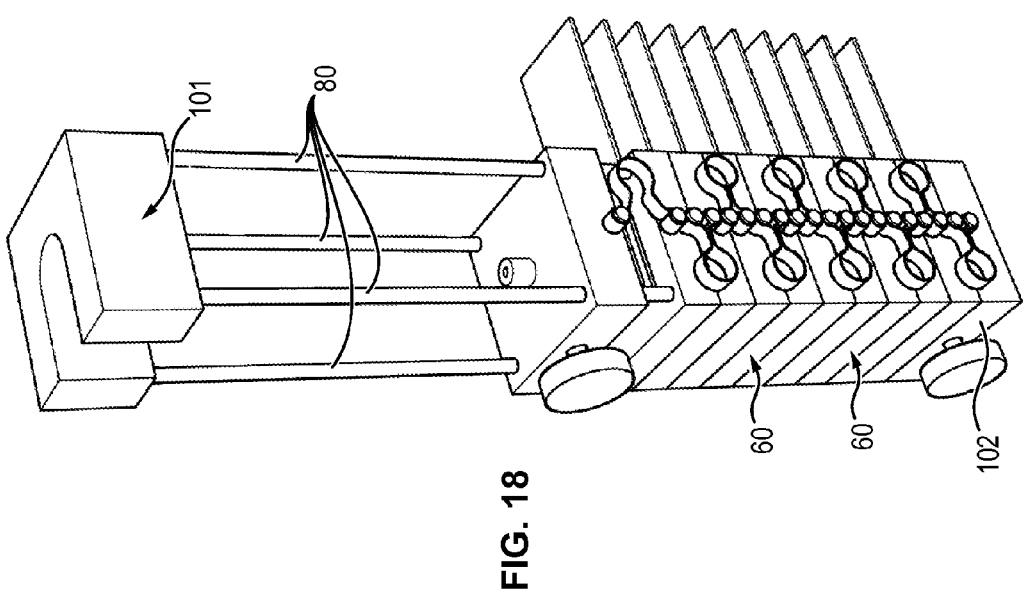
Figure 20:
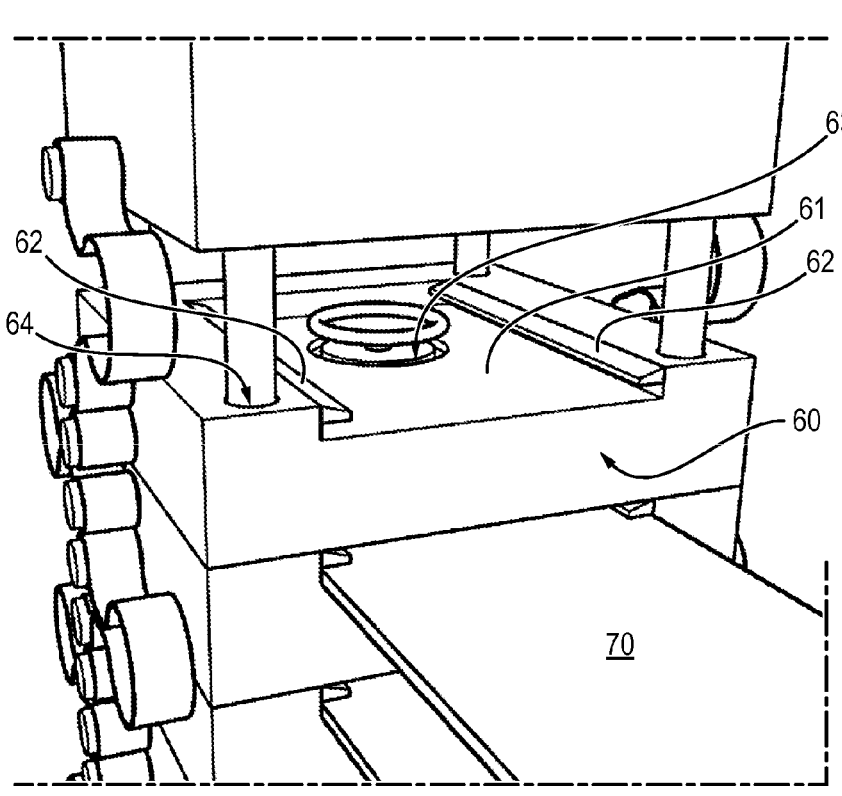

According to an embodiment illustrated in FIGS. 18, 19 and 20, several racks 60 stacked one on top of the other with a blade 70 similar to that described above may be provided. These racks 60 take the form of blocks comprising a slot 61 for inserting the blade 70 on which filtration means 20 are inserted. The blade 70 is inserted into grooves 62. A port 63 in the center of the block allows the fluid to flow through as described above.

Unlike the racks already described, instead of clipping the racks together and in order to improve the mechanical strength of the assembly formed by all the racks, the racks are held by rods 80 forming a block of racks. Preferably, four rods 80 are provided and pass through the racks 70 which include ports 64 in the corners of the racks 70. In order to hold the racks 70 together, foils 90 formed by metal strips hold the racks 70 in pairs. The foils 90 act as springs and allow the racks to be released easily once they are no longer under stress. The foils are attached to two stacked racks by means of arms 65 which protrude from the sides of each rack 70.

In effect, to hold the racks together despite the foils, holding blocks 101, 102 are provided which enclose the rack column, an upper holding block 101 and a lower holding block 102.

In the case of the second and third type compartments, each blade can optionally support multiple filtration means on the same plane in order to have multiple cell types captured by the same blade or a larger number of cells captured on the same blade.

Method

In one aspect, the invention relates to a method for capturing and detecting cells circulating in a fluid in relation to FIG. 21.

A capture method may include a step of applying an electrical signal to the electrodes having a frequency such that an electric field created by the electrodes enables captured cells to be captured or released from the pores due to the dielectrophoretic force generated between the electrodes.

For the capture and detection, a fluid is flowing through the system described above (step E1).

A capture method may include a step of applying an electrical signal to the electrodes having a frequency such that an electric field created by the electrodes enables captured cells to be captured in the pores by the dielectrophoretic force generated between the electrodes (step E2).

Advantageously, the polarization frequency induces a positive dielectrophoretic force during the capture so as to center the cells between the electrodes and to retain the cells in the pores.

To detach the cells, a fluid is flowing through the above system in a direction opposite to that used for the capture (step E3).

After the capture, it is advantageous to be able to detach cells. Thus, the method includes a step of applying an electrical signal to the electrodes having a frequency such that an electric field created by the electrodes allows the release of captured cells in the pores due to the dielectrophoretic force generated between the electrodes (step E4).

To this end, the polarization frequency induces a negative dielectrophoretic force to detach all captured cells, the frequency being typically at 1 MHz.

After the capture and to detach only tumor cells, the frequency induces a dielectrophoretic force to selectively detach one cell type, the frequency being between 50 KHz and 150 kHz, preferably at 100 kHz to detach tumor cells.

Also, after the capture, the polarization frequency is increased in steps between 10 KHz and 200 kHz in order to detach cells at different times depending on their dielectric properties.

The invention claimed is:

1. A system for detecting at least one species present in a fluid, preferably at least one circulating cell or cell aggregate present in a human or animal biological fluid, and in particular circulating tumor cells (CTC) present in a blood fluid: comprising a filter (20) for said fluid, the filter (20) comprising a planar support supporting a filtering membrane, said filtering membrane comprising at least one pore (22) adapted to retain a species of a given type present in the fluid, the filter (20) comprising at least one opening (23) formed in the planar support at the periphery of the at least one pore, the opening being adapted to ensure, in operation within the fluid, a continuity of circulation of the biological fluid through the system even when said at least one pore (22) is occupied.

2. The system of claim 1, comprising a plurality of electrodes (26) arranged around said at least one pore (22), said electrodes forming one or more electrical circuits polarized by an AC electrical signal allowing the measurement of complex impedance variations between these electrodes, as soon as one or more cells are housed in or near a pore (22), the measurement of the variation of the complex impedance modulus and its phase allowing to discriminate the type of cells.

3. The system of claim 2, wherein the AC electrical signal applied to the electrodes has a frequency such that an electric field created by the electrodes enables the capture or release of cells in the pores by virtue of the dielectrophoretic force generated between the electrodes.

4. The system of claim 3, wherein the polarization frequency induces a positive dielectrophoretic force during the capture so as to center the cells between the electrodes and to retain the cells in the pores.

5. The system of claim 3, wherein the polarization frequency induces a negative dielectrophoretic force to detach all captured cells, the frequency being typically at 1 MHz.

6. The system of claim 3, wherein the frequency induces a dielectrophoretic force to selectively detach a cell type, the frequency being between 50 KHz and 150 kHz, preferably at 100 kHz for detaching the tumor cells.

7. The system of claim 3, wherein the polarization frequency is increased in steps between 10 KHz and 200 kHz in order to detach the captured cells at different times depending on their dielectric properties.

8. The system of claim 7, further comprising an inductor (151) connected to the electrodes so as to form an electromagnetic resonator circuit, the electrodes and inductor forming a circuit for detecting, preferably remotely searchable, the presence of trapped cells.

9. The system of claim 1, wherein the filtering membrane (21) is made of a material selected from the group comprising glass or metal, e.g. Nickel, Gold or polymer, ferromagnetic material, magnetic material, e.g. NiFe, or the combination of glass and Silicon or Nickel and Silicon, Silicon Nitride, Silicon Oxide, Silicon or more generally a biocompatible and non-toxic material.

10. The system of claim 1, wherein the pores (22) have a cross-sectional dimension of between 0.1 µm and 100 µm, preferably between 8 µm and 12 µm or between 8 µm and 15 µm; and/or the pores (22) are spaced at an interval of between 100 nm and 100 µm;

the number of pores (22) is between 100 and 100 000 000.

11. The system of claim 1, wherein the pores (22) are substantially circular or substantially oval or substantially polygonal or slit-shaped, said pores preferably being circular.

12. The system of claim 1, wherein the pores (22) of the membrane are arranged in groups of several pores, each group having a pattern, and the groups can be connected to each other via a row of pores.

13. The system of claim 12, wherein the pattern formed by a group has a shape: hexagonal, circular.

14. The system of claim 12, wherein the membrane (21) comprises several groups of pores arranged in a square or star-shaped structure.

15. The system of claim 1, wherein the pores (22) of the membrane are randomly arranged.

16. The system of claim 1, comprising a compartment (30) housing the filter (20), the compartment (30) comprising an inlet module (31) and an outlet module (32) joined together to allow fluid to flow from the inlet module to the outlet module passing through the filter (20).

17. The system of claim 1, comprising an inlet rack (41) and an outlet rack (42), a blade (50) supporting the filter (20), the inlet rack (41) and the outlet rack (42) being joined together so that the blade (50) is between the inlet rack (41) and the outlet rack (42) to allow fluid to flow from the inlet rack (41) to the outlet rack (42) passing through the filter (20).

18. A capture assembly comprising a plurality of systems according to claim 1, arranged in series, each system comprising one or more filters adapted to retain one type of species.

19. The assembly of claim 18, comprising an inlet module, an outlet module, and at least one intermediate module arranged between the inlet module and the outlet module, the intermediate module and the outlet module supporting one or more filters, said modules comprising one or more threadings for fixing them together.

20. The assembly of claim 18, comprising an input rack, an output rack, and at least one intermediate rack arranged between the input rack and the output rack, the intermediate rack and the output rack supporting one or more filters, said racks comprising one or more flexible tabs for fixing them together to form a unitary assembly.

21. A method for capturing cells circulating in a fluid, comprising circulating a fluid in a system according to claim 1, the method comprising applying an electrical signal to electrodes having a frequency such that an electric field created by the electrodes enables captured cells to be captured or released from the pores by virtue of the dielectrophoretic force generated between the electrodes.

22. The capture method of claim 21, wherein the polarization frequency induces a positive dielectrophoretic force during the capture so as to center the cells between the electrodes and to retain the cells in the pores.

23. The capture method of claim 21, wherein the polarization frequency induces a negative dielectrophoretic force to detach all captured cells, the frequency being typically at 1 MHz.

24. The capture method of claim 21, wherein the frequency induces a dielectrophoretic force to selectively detach a cell type, the frequency being between 50 KHz and 150 kHz, preferably at 100 kHz for detaching the tumor cells.

25. The capture method of claim 21, wherein the polarization frequency is increased in steps between 10 KHz and 200 kHz in order to detach the captured cells at different times depending on their dielectric properties.

* * * * *